United States Patent [19]

Karjalainen et al.

[11] Patent Number: 5,559,141
[45] Date of Patent: Sep. 24, 1996

[54] SELECTIVE AROMATASE INHIBITING 4(5)-IMIDAZOLES

[75] Inventors: Arto J. Karjalainen; Marja-Liisa Sodervall; Arja M. Kalapudas; Reino O. Pelkonen, all of Oulu; Aire M. Laine, Turku; Risto A. Lammintausta, Turku; Jarmo S. Salonen, Turku, all of Finland

[73] Assignee: Orion-yhtyma Oy, Espoo, Finland

[21] Appl. No.: 167,873

[22] PCT Filed: Jun. 12, 1992

[86] PCT No.: PCT/FI92/00184

§ 371 Date: May 9, 1994

§ 102(e) Date: May 9, 1994

[87] PCT Pub. No.: WO92/22537

PCT Pub. Date: Dec. 23, 1992

[30] Foreign Application Priority Data

Jun. 18, 1991 [GB] United Kingdom .................... 9113142
Dec. 5, 1991 [GB] United Kingdom .................... 9125924

[51] Int. Cl.⁶ ...................... A61K 31/415; C07D 233/64
[52] U.S. Cl. ...................... 514/400; 514/396; 548/336.1
[58] Field of Search ................. 514/396, 400; 548/336.1

[56] References Cited

U.S. PATENT DOCUMENTS 5,439,928  8/1995  Karjalainen et al. .................. 514/400

FOREIGN PATENT DOCUMENTS

0165779A1  12/1985  European Pat. Off. .
0311447A1   4/1989  European Pat. Off. .
0390558A1  10/1990  European Pat. Off. .

Primary Examiner—Patricia L. Morris
Attorney, Agent, or Firm—Ronald J. Kubovcik

[57] ABSTRACT

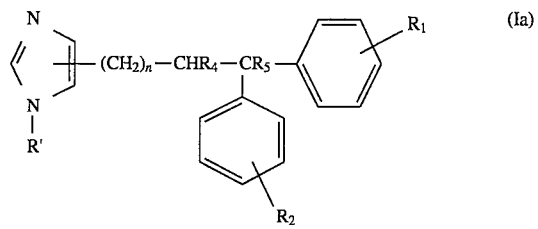

(Ia)

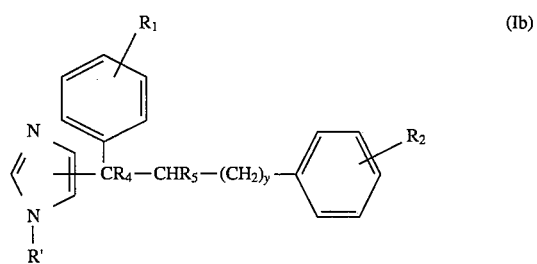

(Ib)

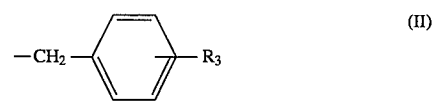

(II)

New 4(5)-imidazole derivatives of formula (Ia) and (Ib) wherein one of $R_1$ and $R_2$ is CN and the other one is H, $CH_3$, $OCH_3$, $NO_2$, $NH_2$, CN, $CF_3$, $CHF_2$, $CH_2F$ or halogen; R' is H or (II) where $R_3$ is H, $CH_3$ or halogen; $R_4$ is H and $R_5$ is H or $R_4$ and $R_5$ together form a bond, n is 1 or 2 and y is 0 to 2, their stereoisomers and their non-toxic pharmaceutically acceptable acid addition salts exhibit selective aromatase inhibiting properties, compared with their desmolase inhibiting properties. The compounds of the invention are valuable in the treatment of estrogen dependent diseases, e.g. breast cancer or benign prostatic hyperplasia (BPH).

24 Claims, No Drawings

SELECTIVE AROMATASE INHIBITING 4(5)-IMIDAZOLES

The present invention relates to substituted imidazole derivatives, their stereoisomers and their non-toxic, pharmaceutically acceptable acid addition salts, and their preparation, to pharmaceutical compositions containing the same and their use.

The imidazole derivatives of the present invention have the general formulae (Ia) or (Ib):

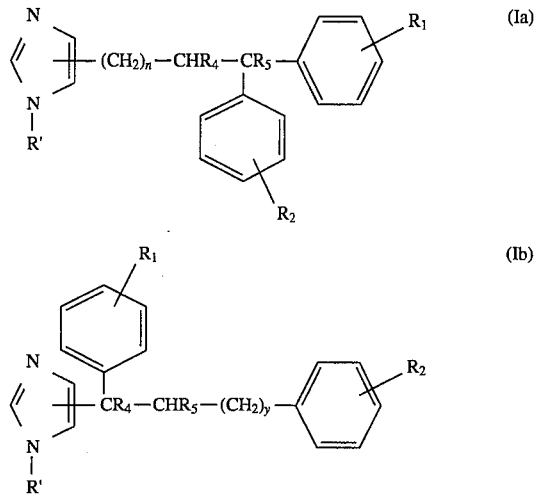

wherein one of $R_1$ and $R_2$ is CN and the other is H, $CH_3$, $OCH_3$, $NO_2$, $NH_2$, CN, $CF_3$, $CHF_2$, $Ch_2F$ or halogen; R' is H or

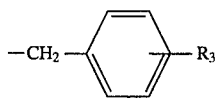

where $R_3$ is H, $CH_3$ or halogen; $R_4$ is H and $R_5$ is H or $R_4$ and $R_5$ together form a bond, n is 1 or 2 and y is 0, 1 or 2.

The compounds of formulae (Ia) and (Ib) are preferably para-substituted and preferably R' is H. For compounds of formula (Ia) preferably $R_1$ is CN and $R_2$ is H, CN, $CF_3$, $OCH_3$ or halogen; especially CN or F. For compounds of formula (Ib) preferably $R_1$ and $R_2$ are both CN or the substituent that is not CN is H or halogen; especially F; more preferably $R_1$ is CN and $R_2$ is H or halogen, especially F. Preferably y is 1 or 2.

The stereoisomers and the non-toxic pharmaceutically acceptable acid addition salts of these compounds are also within the scope of the invention.

The compounds of formulae (Ia) and (Ib) and their stereoisomers form acid addition salts with both organic and inorganic acids. They can thus form many pharmaceutically usable acid addition salts, as for instance, chlorides, bromides, surfaces, nitrates, phosphates, suffonates, formates, tartrates, maleates, citrates, benzoates, salicylates, ascorbates and the like.

The invention includes within its scope pharmaceutical compositions comprising at least some of the compounds of formula (Ia) and (Ib), their stereoisomers or a non-toxic, pharmaceutically acceptable salt thereof, and a compatible pharmaceutically acceptable carrier therefor.

EP-A-0311447 describes diphenyl substituted imidazole derivatives which are stated to be aromatase inhibitors. Compounds in which a phenyl ring is substituted by a cyano group are not disclosed. EP-A-0390558 describes diphenyl substituted imidazole derivatives which are stated to be aromatase inhibitors. Compounds in which a phenyl ring is substituted by a cyano group are not specifically disclosed or exemplified; nor are any test data given for such compounds.

The compounds of the present invention possess selective aromatase inhibiting properties, compared with their desmolase inhibiting properties, and are valuable in the treatment of estrogen dependent diseases, e.g. breast cancer or benign prostatic hyperplasia (BPH). Moreover the compounds of the present invention are unexpectedly more potent aromatase inhibitors than corresponding compounds having no CN substituent(s) in the phenyl ring(s). Interestingly the selectivity of the unsaturated compounds of formulae (Ia) and (Ib) seems to be regulated by the geometric isomerism so that the selectivity ratio of certain configurations is more than one thousand.

Compounds of formula (Ia) can be prepared by reacting a ketone of the formula (IIa)

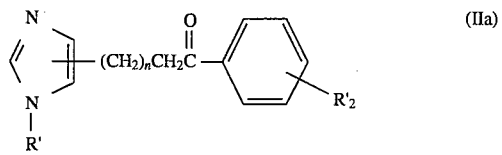

wherein R' is a protecting benzyl group, n is 1 to 2 and $R'_2$ is H, $CH_3$, $OCH_3$, $CF_3$, $CHF_2$, $CH_2F$ or halogen, with an appropriate reagent of the formula (IIIa)

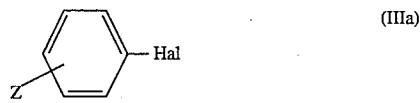

wherein Hal is halogen, especially bromide, and Z is a protecting group, such as a tenbutylaminocarbonyl group, —CONHC(CH$_3$)$_3$, or an oxazoline group, in an appropriate solvent, e.g. tetrahydrofuran, in the presence of an alkyl lithium, for example n-butyl lithium, or magnesium to give compounds of formula (IVa)

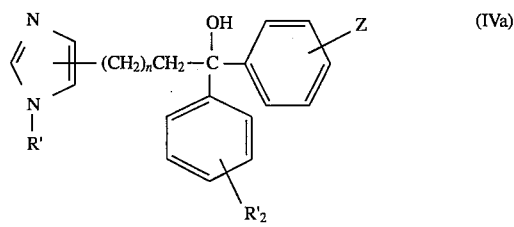

wherein Z, $R'_2$, R' and n are as defined for formulae (II) and (IIIa). Compounds of formula (IVa) are further dehydrated by refluxing with e.g. $SOCl_2$, $POCl_3$ or $PCl_5$ optionally in an appropriate solvent such as acetonitrile. The protecting group Z reacts at the same time to form compounds of formula (Va)

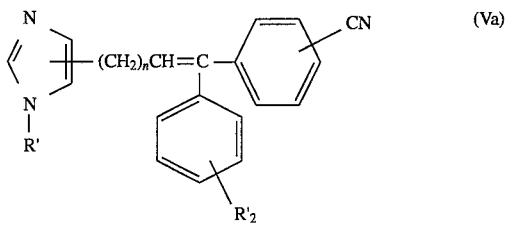

wherein R', n and $R'_2$ are as defined for formula (IIa). The unsaturated compounds (Va) an isolated and then hydrogenated. Alternatively they can be hydrogenated directly in an acidic medium without previous isolation. The hydrogenation is conveniently carried out at room temperature with good stirring in alcohol e.g. ethanol in the presence of a catalyst in a hydrogen atmosphere. Suitable catalysts are for example platinium oxide, palladium-on-carbon or Raney-nickel.

The reaction scheme for this step can be illustrated as follows:

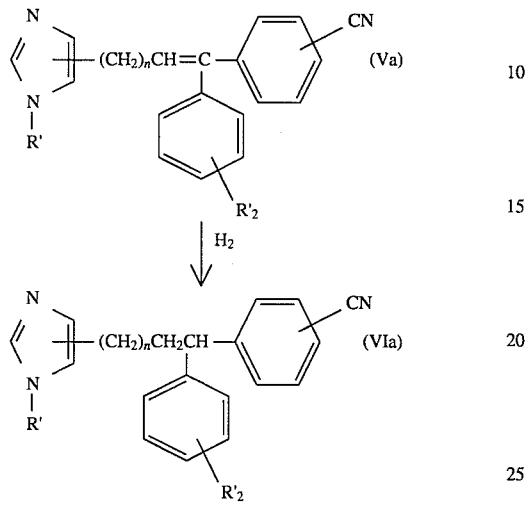

wherein R'$_2$, R' and n are as defined for formula (Va).

The substituted or unsubstituted benzyl group R' may be removed by hydrogenation as well. In this case the hydrogenation is performed in an acidic medium such as hydrochloric acid-ethanol mixture. The reaction scheme of this hydrogenation which leads to compounds of formula (Ia) wherein R', R$_4$ and R$_5$ each are hydrogen can be illustrated as follows:

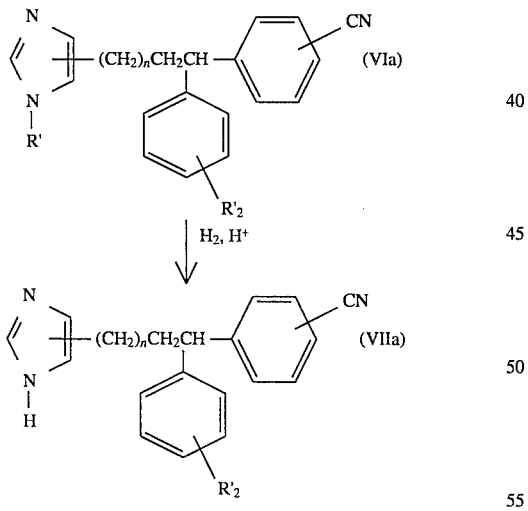

wherein R'$_2$ and n are as defined for formula (Va).

The ketone of formula (IIa) (n=1) may be prepared for example from an 4(5)-imidazole aldehyde and an appropriate acetophenone by aldol condensation and hydrogenation.

The compounds (VIIa) can also be prepared directly from compounds (Va) by hydrogenating both the double bond and the protecting benzyl group at the same time. Another method to remove the benzylic R' group is to react compounds of formula (IVa) by a hydrogen transfer reaction in which the starting compound (IVa) is refluxed with ammonium formate and 10% Pd/C in an appropriate alcohol, such as methanol or ethanol, or its aqueous solution. The reaction scheme can be illustrated as follows:

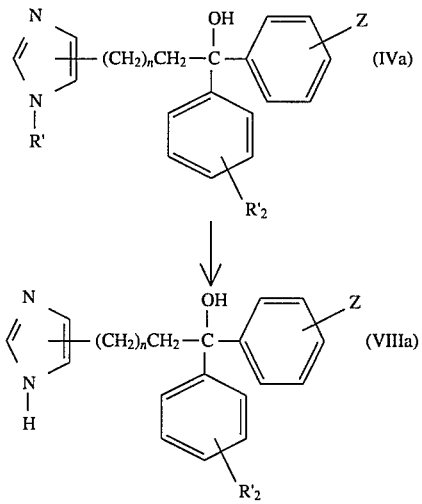

wherein Z, R'$_2$ and n are as defined for formulae (IIa) and (IIIa).

The compounds of formula (VIIIa) are further dehydrated and hydrogenated as described before to form the compounds of formula (VIIa).

Another method to give compounds of formula (Ia) is refluxing compounds of formula (IVa) or (VIIIa) in an appropriate solvent, such as dichloromethane, in the presence of SOCl$_2$ to give compounds of formula (IXa)

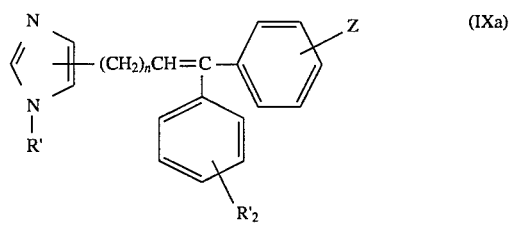

wherein R' is H or a protecting group and Z, R'$_2$ and n are as defined for formula (IVa). The compounds of formula (IXa) are further matched by hydrogen transfer reaction or hydrogenareal to give compounds of formula (Xa)

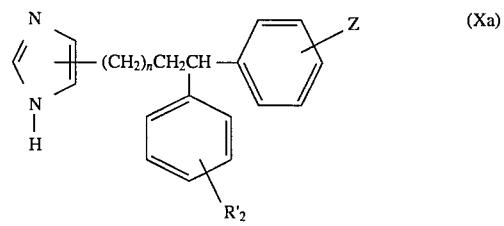

wherein Z, R'$_2$ and n are as defined for formula (IVa). Compounds of formula (Xa) are further reacted with SOCl$_2$ to give compounds of formula (VIIa).

Compounds of formula (Xa) can also be prepared by a hydrogen transfer reaction from compounds of formula (IVa) in which the starting compound (IVa) is refluxed with ammonium formate and 10% Pd/C in an acidic medium, such as acetic acid.

Compounds of formula (Ia) wherein $R_2$ is $R_1$ can be prepared by reacting an ester of formula (XIa)

(XIa)

wherein R' is a protecting benzyl group, n is 1 to 2 and R is a lower alkyl group, especially $C_1$–$C_3$-alkyl, with the reagent (IIIa) in an appropriate solvent, e.g. tetrahydrofuran, in the presence of an alkyl lithium, e.g. n-butyl lithium, or magnesium to give compounds of formula (XIIa)

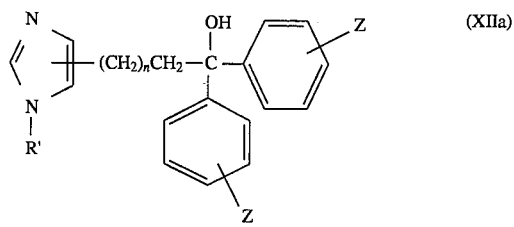
(XIIa)

wherein R', n and Z are as defined for formulae (XIa) and (IIIa). Compounds of formula (XIIa) are further reacted by the ways described before to give compounds of formula (XIIIa)

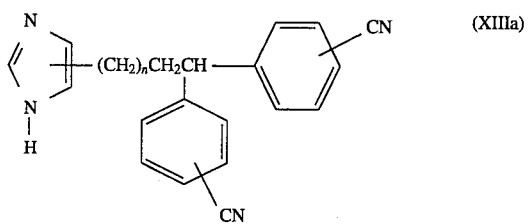
(XIIIa)

wherein n is 1 to 2.

The starting compound of formula (XIa) may be prepared for example by esterfiying the corresponding acid in the usual way.

Compounds of formula (XIIa) can also be prepared by a Grignard reaction which comprises refluxing in a suitable solvent an ester of formula (XIa) with a Grignard reagent (XIVa)

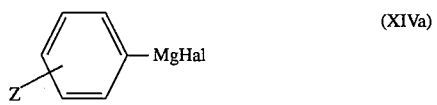
(XIVa)

wherein Hal is halogen, especially bromide, and Z is an oxazoline group. The Grignard reagent is prepared by reacting the corresponding halide derivative with magnesium. Suitable solvents for the reaction include a variety of ethers, preferably tetrahydrofuran.

Compounds of formula (Ia) wherein the substituent(s) is(are) CN can be prepared from the corresponding compounds where the substituent(s) is(are) $NH_2$ by diazotization.

Compounds of formula (Ia) wherein the substituent(s) is(are) $NH_2$ can be prepared by hydrogenating the corresponding compounds where the substituent(s) is(are) $NO_2$. Compounds of formula (Ia) wherein the substituent(s) is(are) $NO_2$ can be prepared by nitration.

Compounds of formula (Ib) can be prepared by a successive sequence of reactions comprising firstly a reaction of 4(5)-imidazole aldehyde (IIb)

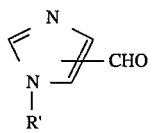
(IIb)

wherein R' is a protecting benzyl group, with an arylalkylhalide (IIIb)

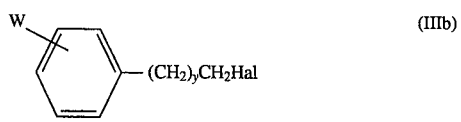
(IIIb)

wherein Hal is halogen, y is 0 to 2 and W is $R'_2$ or Z. $R'_2$ is H, $CH_3$, $OCH_3$, $CF_3$, $CHF_2$, $CH_2F$ or halogen and Z is a protecting group, such as a tert-butylaminocarbonyl group, $-CONHC(CH_3)_3$, or all oxazoline group in the presence of magnesium or an alkyl lithium, such as n-butyl lithium. This reaction leads to following compounds (IVb)

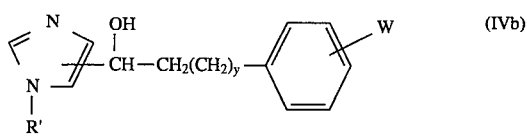
(IVb)

In the reaction the arylalkylhalide derivative can be, for example, an arylalkylbromide derivative. Suitable solvents for the reaction include a variety of ethers, preferably tetrahydrofuran.

Compounds of formula (IVb) are further oxidized for example with manganese dioxide to achieve compounds of formula (Vb) which are allowed to react with an appropriate halide derivative (VIb) in an appropriate solvent, such as tetrahydrofuran, in the presence of an alkyl lithium, for example n-butyl lithium, or magnesium to give the compounds of formula (VIIb) wherein R', y, W and Z are as defined for formulae (IIb) and (IIIb). The reaction scheme for these steps can be illustrated as follows:

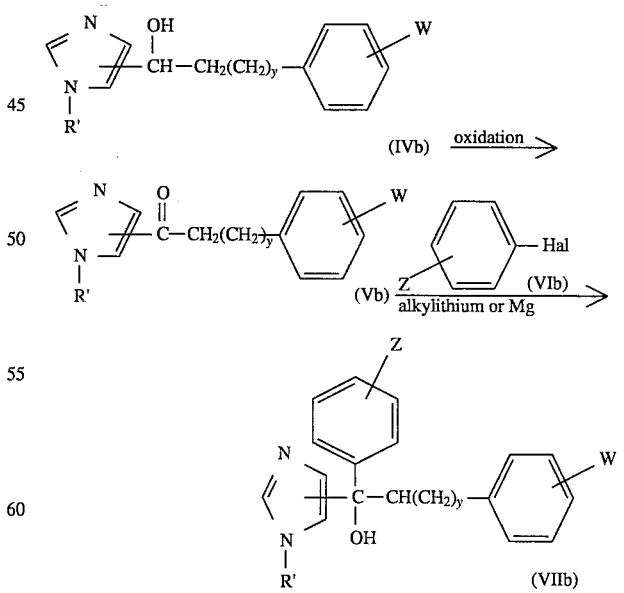

Compounds of formula (VIIb) are further refluxed with e.g. $SOCl_2$, $POCl_3$ or $PCl_5$, optionally in an appropriate solvent, such as acetonitrile, to give compounds of formula (VIIIb)

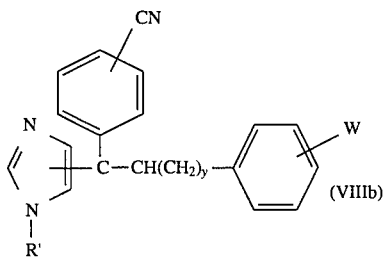

wherein R' and y are as defined before and W is CN or R'$_2$.

Compounds of formula (Vb) where W is R'$_2$ may also be prepared by aldol condensation of an 4(5)-acetylimidazole with an appropriate aldehyde followed by hydrogenation of the condensation product.

The unsaturated compounds (IIIb) are isolated and then hydrogenated. Alternatively they can be hydrogenated directly in an acidic medium without previous isolation. The hydrogenation is conveniently carried out at room temperature with good stirring in alcohol, e.g. ethanol, in the presence of a catalyst in a hydrogen atmosphere. Suitable catalysts are for example platinium oxide, palladium-on-carbon or Raney-nickel.

The reaction scheme for this step can be illustrated as follows:

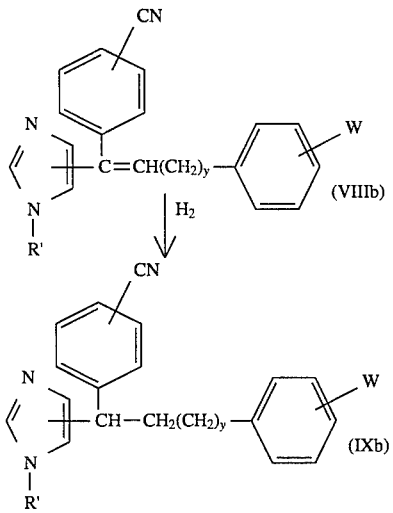

wherein R', y and W are as defined for formula (VIIIb).

The substituted or unsubstituted benzyl group R' may be removed by hydrogenation as well. In this case the hydrogenation is performed in an acidic medium such as hydrochloric acid-ethanol mixture. The reaction scheme for this hydrogenation which leads to compounds of formula (Ib) wherein R', R$_4$ and R$_5$ are hydrogen can be illustrated as follows:

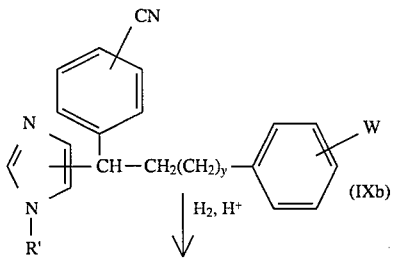

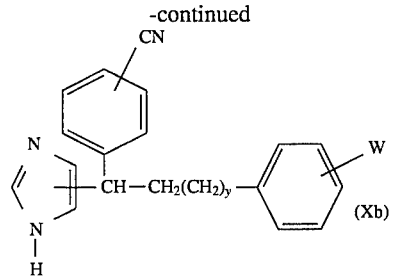

wherein W is as defined for formula (VIIIb).

The compounds of formula (Xb) can also be prepared directly from compounds (VIIIb) by hydrogenating both the double bond and the protecting benzyl group at the same time. Another method to remove the benzylic R' group is to react compounds of formula (VIIb) by a hydrogen transfer teation in which the starting compound (VIIb) is refluxed with ammonium formate and 10% Pd/C in an appropriate alcohol, such as methanol or ethanol, or its aqueous solution. The reaction scheme can be illustrated as follows:

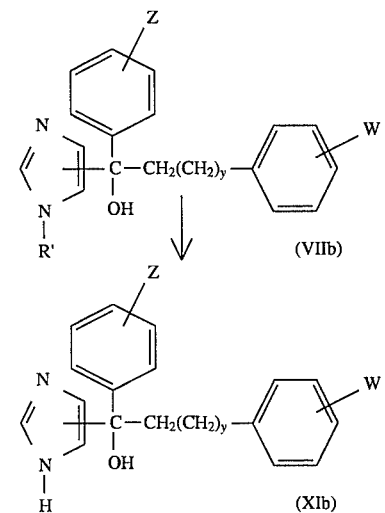

wherein Z is a protecting group as defined before, W is Z or R'$_2$ and y is 0 to 2.

The compounds of formula (XIb) are further dehydrated as described before to form the compounds of formula (XIIb)

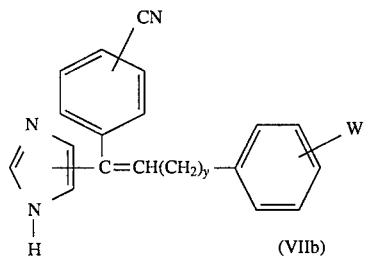

wherein W is CN or R'$_2$ and y is 0 to 2.

Compounds of formulae (VIIIb) and (XIIb) wherein W is CN or R'$_2$ may also be prepared from compounds of formulae (VIIb) and (XIb) wherein Z is an oxazole group and W is an oxazole group or R'$_2$ by allowing the compounds to react with an appropriate mineral acid, converting the formed acid group(s) into amide group(s) by usual methods and further refluxing with e.g. SOCl$_2$, POCl$_3$ or PCl$_5$ optionally in an appropriate solvent Compounds of formula (Va) wherein R' is H or a protecting benzyl group may be prepared by the same method from compounds of formulae (IVa) and (VIIIa) wherein Z is an oxazoline group and R'₂ is as defined before. Also the corresponding dicyanosubstituted compounds may be prepared by the same method.

Another method to give compounds of formula (Ib) is refluxing compounds of formula (VIIb) or (XIb) in an appropriate solvent, such as dichloromethane, in the presence of SOCl₂ to give compounds of formula (XIIIb)

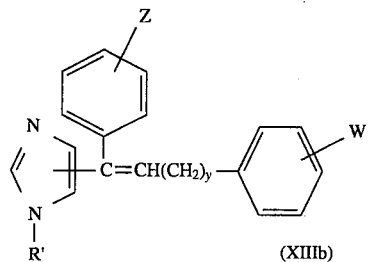

(XIIIb)

wherein R' is H or a protecting group and Z, W and y are as defined for formula (XIb). The compounds of formula (XIIIb) are further reacted by a hydrogen transfer reaction or hydrogenated to give compounds of formula (XIVb)

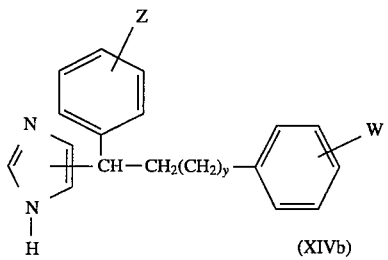

(XIVb)

wherein Z, W and y are as defined for formula (XIb). Compounds of formula (XIVb) are further reacted with e.g. SOCl₂ to give compounds of formula (Xb).

Compounds of formula (XIVb) can also be prepared by a hydrogen transfer reaction from compounds of formula (VIIb) in which the starting compound (VIIb) is refluxed with ammonium formate and 10% Pd/C in an acidic medium, such as acetic acid.

Compounds of formula (Ib) can also be prepared by reacting an 4(5)-imidazole aldehyde (IIb) with an arylalkyl halide (XVb)

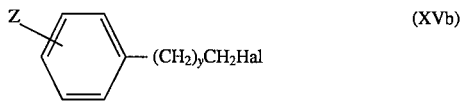

(XVb)

wherein y is 0 to 2 and Z is a protecting group, such as a tert-butylaminocarbonyl group or an oxazoline group, in the presence of magnesium or an alkyl lithium, such as n-butyl lithium, which leads to following compounds (XVIb)

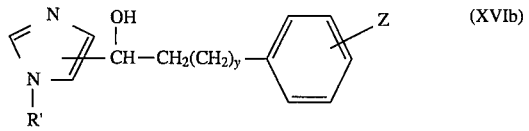

(XVIb)

wherein R' is a protecting benzyl group. The compounds of formula (XVIb) are further oxidized to form compounds of formula (XVIIb)

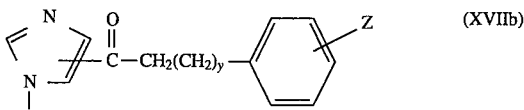

(XVIIb)

which are further allowed to react with an appropriate halide derivative (XVIIIb)

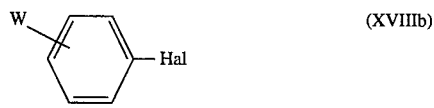

(XVIIIb)

wherein W is Z or R'₂. R'₂ is H, CH₃, OCH₃, CF₃, CHF₂, CH₂F or halogen. The reaction is carried out in an appropriate solvent, such as tetrahydrofuran, in the presence of an alkyl lithium, for example n-butyl lithium, or magnesium to give compounds of formula (XIXb)

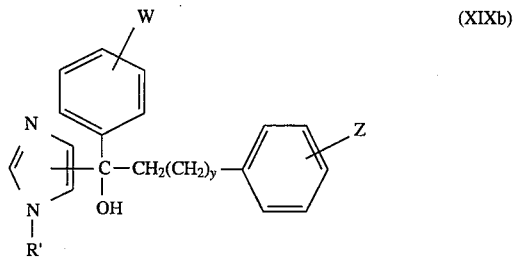

(XIXb)

wherein R', Z, W and y are as defined for formulae (IIb), (XVb) and (XVIIIb). Compounds of formula (XIXb) are further reacted as described before to give compounds of formula (Ib).

Compounds of formula (Ib) wherein the substituent(s) is(are) CN can be prepared from the corresponding compounds where the substituent(s) is(are) NH₂ by diazotization.

Compounds of formula (Ib) wherein the substituent(s) is(are) NH₂ can be prepared by hydrogenating the corresponding compounds where the substutuent(s) is(are) NO₂. Compounds of formula (Ib) wherein the substituent(s) is(are) NO₂ can be prepared by nitration.

The compounds of formula (Ia) and (Ib), their non-toxic, pharmaceutically acceptable acid addition salts or mixtures thereof may be administered parenterally, intravenously or orally. Typically, an effective amount of the compound is combined with a suitable pharmaceutical carrier. As used herein, the term "effective amount" encompasses those amounts which yield the desired activity without causing adverse side-effects. The precise amount employed in a particular situation is dependent upon numerous factors such as method of administration, type of mammal, condition for which the compound is administered, etc., and of course the structure of the compound.

The pharmaceutical carriers which are typically employed with the compounds of the present invention may be solid or liquid and are generally selected with the planned manner of administration in mind. Thus, for example, solid carriers include lactose, sucrose, gelatin and agar, while liquid careers include water, syrup, peanut oil and olive oil. Other combination of the compound and the carrier may be fashioned into numerous acceptable forms, such as tablets, capsules, suppositories, solutions, emulsions and powders.

The compounds of the invention are especially valuable as aromatase inhibiting agents and are therefore useful in the treatment of estrogen dependent diseases, e.g. breast cancer or benign prostatic hyperplasia (BPH).

Estrogens are essential steroids in the physiology and function of normal development of breast and sex organs in women. On the other hand estrogens are known to stimulate the growth of estrogen dependent cancers, especially breast and endometrial cancers, and they may increase the risk of development of breast cancer if given at pharmacological doses for a long time. Excessive production of estradiol may also cause other, benign disorders in hormone dependent organs. The importance of estrogens as cancer growth stimulators and/or regulators is clearly stressed by the fact that antiestrogens have reached a central position in the treatment of estrogen receptor rich breast cancers. Antiestrogens act by binding to estrogen receptors and thereby inhibiting the biological effect of estrogens. This has been achieved clinically by the unspecific steroid synthesis inhibitor aminoglutethimide. The estrogen synthesis could be blocked specifically by inhibiting the enzyme aromatase, which is the key enzyme in biochemical estrogen synthesis pathway. Aromatase inhibition is important because several breast tumors synthesize estradiol and estrone in situ and exhibit therefore continuous growth stimulation (Alan Lipton et al., Cancer 59:770–782, 1987).

The ability of the compounds of the invention to inhibit the enzyme aromatase was shown by the in vitro assay method according to M. Pasanen (Biological Research in Pregnancy, vol. 6, No. 2, 1985, pp. 94–99). Human aromatase enzyme was used. The enzyme was prepared from human placenta, which is rich of the enzyme. Microsomal fraction (100000×g precipitate) was prepared by centrifugation. The enzyme preparation was used without further purification. Test compounds listed in Table 1 were added together with 100000 dpm of 1,2[$^3$H]-androstene-3,17-dione and NADPH generating system. The concentrations of the test compounds were 0,001; 0,01; 0,1 and 1,0 mM. The incubation was carried out at 37° C. for 40 min. Aromatization of 1,2[$^3$H]-androstene-3,17-dione results in the production of $^3$H$_2$O. The tritiated water and the tritiated substrate are easily separated by a Sep-Pak™ minicolumn, which absorbs the steroid but allows free water elution. Radioactivity was counted by a liquid scintillation counter. Aromatase inhibition was evaluated by comparing the $^3$H$_2$O-radioactivity of inhibitor treated samples to controls containing no inhibitor. IC-50 values were calculated as concentrations which inhibited the enzyme activity 50%. These concentrations are presented in Table 2.

Cholesterol side chain cleavage (SCC) activity (desmolase) was measured according to the method of Pasanen and Pelkonen (Steroids 43:517–527, 1984). Incubations were carried out in 1,5 ml Eppendorf plastic tubes, and an Eppendorf shaker, centrifuge and incubator were used as a unit. In a 300 µl incubation volume, the substrate (5 µM) was prepared according to Hanukoglu and Jefcoate (J. Chromatogr. 190:256–262, 1980), and 100000 dpm of radioactive $^3$H-4-cholesterol (the purity of the compound was checked by TLC) in 0,5% Tween 20, 10 mM MgCl$_2$, 5 µM cyanoketone and 2 mM NADPH was added. Controls contained all the above substances but the enzyme preparation was inactivated prior to the incubation by the addition of 900 µof methanol. The mitochondrial fraction (1 mg protein) from human placenta or bovine adrenals was used as a source of enzyme. After 30 min incubation at 37° C., the reaction was terminated by the addition of 900 µl of methanol; 1500 dpm of marker $^{14}$C-4-pregnenolone was added to each incubate and the tubes were vigorously shaken. After 10 min equilibration, the methanol-precipitated proteins were separated by centrifugation (8000×g for 2 min) and the supernalant was sucked into 1 ml plastic injection syringe and loaded onto the pre-equilibrated (75% methanol) minicolumn. The column was washed with one ml of 75% methanol and then with 3 ml of 80% methanol. The 80% methanol eluate was run into the counting vial and 10 ml of scintillation liquid was added. Radioactivity was counted using a double-label program on a liquid scintillation counter (LKB RackBeta). Typical activities for placental and bovine adrenal enzyme preparation were 0,5–3 and 50–100 pmol pregnenolone formed/mg protein/min, respectively.

In inhibition experiments, the substance (final concentration range from 1 to 1000 µM) was added into incubation mixture in a volume of 10–20 µl, usually as methanol or ethanol solution. The same volume of the solute was added into control incubation vial. The IC-50 values (concentration causing a 50% inhibition) were determined graphically and are presented in Table 2.

In the tables the unsaturated geometric isomers are described by letters a and b.

TABLE 1

Compounds tested

| No. | Name |
| --- | --- |
| 1a. | 4-[3-(4-cyanophenyl)-3-phenylpropyl]-1H-imidazole |
| 2a. | 4-[3,3-bis(4-cyanophenyl)propyl]-1H-imidazole |
| 3a. | 4-[3-(4-cyanophenyl)-3-(4-fluorophenyl)propyl]-1H-imidazole |
| 4a. | 4-[3-(4-cyanophenyl)-3-(4-fluorophenyl)-2-propenyl]-1H-imidazole |
| 5a. | 1-benzyl-5-[3,3-bis(4-cyanophenyl)-2-propenyl]-1H-imidazole |
| 6a. | 4-[4,4-bis(4-cyanophenyl)butyl]-1H-imidazole |
| 7a. | 1-benzyl-5-[4,4-bis(4-cyanophenyl)butyl]-1H-imidazole |
| 8a. | 4-[3,3-bis(4-cyanophenyl)-2-propenyl]-1H-imidazole |
| 9a. | 4-[3-(4-cyanophenyl)-3-(4-trifluoromethylphenyl)propyl]-1H-imidazole |
| 10a. | 4-[3-(4-cyanophenyl)-3-(4-methoxyphenyl)propyl]-1H-imidazole |
| 1b. | 4-[1-(4-cyanophenyl)-4-phenylbutyl]-1H-imidazole |
| 2b. | 4-[1-(4-cyanophenyl)-4-(4-fluorophenyl)butyl]-1H-imidazole |
| 3b. | 4-[1-(4-cyanophenyl)-4-(4-fluorophenyl)-1-butenyl]-1H-imidazole |
| 4b. | 4-[1-(4-cyanophenyl)-4-(4-fluorophenyl)-1-butenyl]-1H-imidazole, isomer a |
| 5b. | 4-[1-(4-cyanophenyl)-4-(4-fluorophenyl)-1-butenyl]-1H-imidazole, isomer b |
| 6b. | 4-[1-(4-cyanophenyl)-3-(4-fluorophenyl)-1-propenyl]-1H-imidazole, isomer a |
| 7b. | 4-[1-(4-cyanophenyl)-3-(4-fluorophenyl)-1-propenyl]-1H-imidazole, isomer b |
| 8b. | 4-[3-(4-cyanophenyl)-1-(4-fluorophenyl)-1-propenyl]-1H-imidazole |
| 9b. | 4-[1,4-bis(4-cyanophenyl)-1-butenyl]-1H-imidazole |

TABLE 2

Inhibition of human aromatase and desmolase by test compounds. IC-50 represents the concentration which inhibits the enzyme 50%.

| Compound No. | AROMATASE IC-50 µmol/l | DESMOLASE IC-50 µmol/l |
| --- | --- | --- |
| 1a. | 0, 48 | 14 |
| 2a. | 0, 86 | 36 |
| 3a. | 0, 41 | 43 |
| 4a. | 0, 65 | 62 |
| 5a. | 3, 2 | 15, 5 |
| 6a. | 1, 6 | 47 |
| 7a. | 5, 0 | 22 |
| 8a. | 0, 97 | 33 |
| 9a. | 2, 4 | 64 |
| 10a. | 0, 85 | 33 |
| 1b. | 0, 21 | 12 |
| 2b. | 0, 23 | 20 |
| 3b. | <0, 25 | 26 |

TABLE 2-continued

Inhibition of human aromatase and desmolase by test compounds. IC-50 represents the concentration which inhibits the enzyme 50%.

| Compound No. | AROMATASE IC-50 µmol/l | DESMOLASE IC-50 µmol/l |
|---|---|---|
| 4b. | 0, 21 | 33 |
| 5b. | 0, 19 | >1000 |
| 6b. | 0, 19 | 36 |
| 7b. | 0, 33 | 3, 4 |
| 8b. | 1, 0 | 4, 0 |
| 9b. | 1, 1 | 6, 3 |

In general the daily dose for a patient would be from about 20 to about 200 mg, administered orally.

The anti-tumour effect was investigated in vivo against DMBA-induced rat mammary adenocarcinomas by the following method. Mammary adenocarcinoma was induced with DMBA in 50±2 days old female rats. Treatment with the compound under test was started after palpable tumours had appeared. Tumour size and aamount of tumours were evaluated once a week. Tumour sizes in the control group, treated with solvent, were compared with the test groups. Daily administration schedule was employed for five weeks and animals were sacrificed. The change in tumour sizes was evaluated.

Results were evaluated as changes in the sizes of tumours and were divided into four groups: completely remitted tumours, decreasing tumours, stable tumours and growing tumours. The anti-tumour effect of 4-[1-( 4-cyano-phenyl)-4-(4-fluorophenyl)butyl]- 1H-imidazole and 4-[1-(4-cyanophenyl)-3-(4-fluorophenyl)- 1-propenyl]-1H-imidazole isomer a were tested and the results are presented in Table 3 and Table 4.

TABLE 3

Relative number of different tumour types in control and 4-[1-(4-cyanophenyl)-4-(4-fluorophenyl)butyl]-1H-imidazole (test compound 1) treated groups of DMBA-induced mammary tumour rats.

| group | tumours/rat | | effect at the end of treatment tumours/rat | | | |
|---|---|---|---|---|---|---|
| | a | b | CR | PR | NC | P |
| control n = 8 | 2, 3 | 11, 8 | — | — | 0, 3 | 11, 5 |
| test compound 1 5 mg/kg n = 7 | 2, 1 | 3, 0 | — | 1, 4 | 0, 7 | 0, 9 |
| test compound 1 15 mg/kg n = 8 | 3, 3 | 3, 1 | 1, 4 | 1, 4 | 0, 6 | 1, 1 | a: at the beginning
b: at the end of treatment
CR: complete remission
PR: partial remission, decreasing tumours
NC: no change, stable tumours
P: progression, growing tumours

TABLE 4

Relative number of different tumour types in control and 4-[1-(4-cyanophenyl)-3-(4-fluorophenyl)-1-propenyl]-1H-imidazole isomer a (test compound 2) treated groups of DMBA-induced mammary tumour rats.

| group | tumours/rat | | effect at the end of treatment tumours/rat | | | |
|---|---|---|---|---|---|---|
| | a | b | CR | PR | NC | P |
| control n = 6 | 2, 3 | 7, 8 | — | — | — | 7, 8 |
| test compound 2 2 mg/kg n = 6 | 2, 3 | 7, 5 | — | 0, 2 | 0, 2 | 7, 2 |
| test compound 2 7, 5 mg/kg n = 6 | 2, 3 | 3, 3 | — | 0, 8 | 0, 2 | 2, 3 |
| test compound 2 15 mg/kg n = 5 | 2, 2 | 3, 0 | 0, 2 | 2, 0 | — | 1, 0 | a: at the beginning
b: at the end of treatment
CR: complete remission
PR: partial remission, decreasing tumours
NC: no change, stable tumours
P: progression, growing tumours Acute toxicity, $LD_{50}$, was determined by using young adult female mice of NMRI-Stmin. The administration of the test compounds was oral. The $LD_{50}$-value for 4-[3-(4-cyanophenyl)-3-(4-fluorophenyl)propyl]- 1H-imidazole was 210 mg/kg and for 4-[1-(4-cyanophenyl)-3-(4-fluorophenyl)-1-propenyl isomer a was more than 400 mg/kg.

The following examples illustrate the invention.

$^1$H NMR spectra were determined with a Bruker AC-P300 apparatus. The reference substance was tetramethylsilane. MS spectra were determined with Kratos MS80RF Auto-console apparatus.

EXAMPLE 1

4-[3-(4-cyanophenyl)-3-phenylpropyl]- 1H-imidazole a) 1-benzyl-5-[3-(4-tert-butylaminocarbonylphenyl)-3-hydroxy-3-phenyl-propyl]- 1H-imidazole 4-tert-butylammiocarbonylbromobenzene (8,16 g, 32 mmol) is dissolved in dry tetrahydrofuran (240 ml). The solution is cooled to −70° C. 2,5M n-butyl lithium in hexane (25,4 ml, 63,6 mmol) is added to the solution under nitrogen atmosphere keeping the temperature at −70° C. The mixture is stirred for 30 min. 3-(1-benzyl-5-imidazolyl)propiophenone (7,7 g, 26,6 mmol) in 240 ml of THF is added at −70° C. to the reaction mixture. The mixture is stirred and it is allowed to warm up to room temperature. Saturated ammonium chloride solution is added to the reaction mixture and THF is evaporated. The residue is extracted with diethyl ether. The ether extracts axe combined and treated with 2 M HCl. The precipitated hydrochloride salt of the product is filtered off.

$^1$H NMR (as HCl-salt, MeOH-d$_4$):
1.44 (s, 9H), 2.49–2.61 (m, 4H), 5.30 (s, 2H), 7.06–7.11 (m, 2H), 7.17–7.41 (m, 9H), 7.46 (d, 2H), 7.66 (d, 2H), 8.92 (d, 1H)

The following compounds were prepared by the same procedure:

1-benzyl-5-[3-(4-tert-butylaminocarbonylphenyl)-3-(4-fluorophenyl)-3-hydroxypropyl]-1H-imidazole ¹H NMR (as HCl-salt, MeOH-d₄):
1.46 (s, 9H), 2.52 (br s, 4H), 5.20 (s, 2H), 6.97 (t, 2H), 7.05–7.08 (m, 2H), 7.23 (s, 1H), 7.30–7.36 (m, 5H), 7.42 (d, 2H), 7.64 (d, 2H), 8.76 (d, 1H)

1-benzyl-5-[3-(4-tert-butylaminocarbonylphenyl)- 3-(4-trifluoromethylphenyl)-3-hydroxypropyl]- 1H-imidazole ¹H NMR (as HCl-salt, MeOH-d₄):
1.441 (s, 9H), 2.45–2.65 (m, 4H), 5.326 (s, 2H), 7.07–7.11 (m, 2H), 7.32–7.33 (m, 3H), 7.436 (s, 1H), 7.488 (d, 2H), 7.589 (AB q, 4H), 7.686 (d, 2H), 8.954 (d, 1H)

1-benzyl-5-[3-(4-tert-butylaminocarbonylphenyl)- 3-hydroxy-3-(4-methoxyphenyl)propyl]-1H-imidazole ¹H NMR (as HCl-salt, MeOH-d₄):
1.46 (s, 9H), 2.40–2.0 (m, 4H), 3.78 (s, 3H), 6.82 (d, 2H), 7.05–7.07 (m, 2H), 7.21 (s, 1H), 7.25 (d, 2H), 7.34–7.36 (m, 3H), 7.41 (d, 2H), 7.63 (d, 2H), 8.78 (s, 1H)

b) 1-benzyl-5-[3-(4-cyanophenyl)-3-phenyl-2-propenyl]-1H-imidazole 1-benzyl-5-[3-(4-tert-butylaminocarbonylphenyl)- 3-hydroxy-3-phenylpropyl]-1H-imidazole (3,4 g) is heated in SOCl₂ (35 ml) at 70°–80 °C. for 1 h. After the heating thionyl chloride is evaporated. Dilute Na₂CO₃ solution is added to the residue and the product is extracted into ethyl acetate. The organic layer is dried and the solvent is evaporated. Yield 2,48 g, 92%.

The same result is achieved by refluxing the starting compound (1 mmol) with PCl₅ (0.8 mmol) in dry acetonitrile.

¹H NMR (as base, CDCl₃):
3.19 and 3.31 (2d, together 2H), 4.95 and 4.98 (2s, together 2H) 6.12 and 6.17 (2t, together 1H), 6.87–6.92 (m, 3H), 7.15–7.20 (2 overlapping d, together 2H), 7.23–7.38 (m, 6H), 7.51 and 7.57 (2d, together 2H), 7.61 (s, 1H)

By the same method was prepared 1-benzyl-5-[3-( 4-cyanophenyl)-3-(4-fluorophenyl)-2-propenyl]-1H-imidazole.

¹H NMR (as base, CDCl₃):
3.18 and 3.27 (2d, together 2H), 4.98 (s, 2H), 6.11 and 6.15 (2t, together 1H), 6.87–6.90 (m, 3H), 6.96 (t, 2H) 7.02–7.07 (m, 2H), 7.17 and 7.18 (2d, together 2H), 7.27–7.30 (m, 3H), 7.52 and 7.58 (2d, together 2H) under which (s, 1H)

c) 4-[3-(4-cyanophenyl)-3-phenylpropyl]-1H-imidazole 1-benzyl-5-[3-(4-cyanophenyl)-3-phenyl- 2-propenyl]-1H-imidazole hydrochloride is hydrogenated in ethanol using 10% Pd/C as a catalyst.

¹H NMR (as HCl-salt, MeOH-d₄):
2.45–2.54 (m, 2H), 2.69 (dist.t, 2H), 4.11 (t, 1H), 7.18–7.25 (m, 1H), 7.29 (s, 1H), 7.31–7.33 (m, 4H), 7.51 (d, 2H), 7.65 (d, 2H), 8.77 (d, 1H)

MS:287 (12, M³⁰), 190(16), 183 (17), 158(20), 95(12), 82(100)

4-[3-(4-cyanophenyl)-3-(4-fluorophenyl)propyl]-1H-imidazole was also obtained by the same method.

¹H NMR (as HCl-salt, MeOH-d₄):
2.44–2.52 (dist q, 2H), 2.66–2.71 (dist t, 2H), 4.08 (t, 1H), 7.05 (t, 2H), 7.30 (s, 1H), 7.32–7.36 (m, 2H), 7.50 (d, 2H), 7.67 (d, 2H), 8.78 (d, 1H)

MS: 305 (7, M⁺.), 183(14), 95 (7), 82(100)

EXAMPLE 2

4-[3-(4-cyanophenyl)-3-phenylpropyl]-1H-imidazole a) 4-[3-(4-tert-butylaminocarbonylphenyl)- 3-hydroxy-3-phenylpropyl]-1H-imidazole 1-benzyl-5-[3-(4-tert-butylaminocarbonylphenyl)-3-hydroxy-3-phenylpropyl]- 1H-imidazole (3,6 g, 7,7 mmol) is dissolved in aqueous ethanol (80 ml) and 10% Pd/C (0,36 g) is added. Ammonium formate (1,95 g, 31 mmol) is added to the boiling solution. The mixture is refluxed for four hours. After the refluxing the solvents are evaporated. 2M sodium hydroxide is added to the residue and the product is extracted into ethyl acetate, dried and the solvent is evaporated. Yield 2,7 g, 93,5%.

¹H NMR (as base, CDCl₃):
1.40 (s, 9H), 2.45–2.60 (m, 4H), 6.14 (br s, 1H), 6.49 (s, 1H), 7.12–7.53 (m, 10H)

The following compounds were prepared by the same procedure:

4-[3-(4-tert-butylaminocarbonylphenyl)-3-( 4-fluorophenyl)-3-hydroxypropyl]-1H-imidazole ¹H NMR (as base, CDCl₃):
1.41 (s, 9H), 2.52 (m, 4H), 6.10 (br s, 1H), 6.53 (s, 1H), 6.89 (t, 2H), 7.23 (s, 1H), 7.33–7.37 (m, 2H), 7.43 (d, 2H), 7.54 (d, 2H) 4-[3-(4-tert-butylaminocarbonylphenyl )-3-( 4-trifluoromethylphenyl)-3-hydroxypropyl]-1H-imidazole ¹H NMR (as base, CDCl₃+MeOH-d₄):
1.435 (s, 9H), 2.623 (m, 4H), 6.304 (br s, 1H), 6.778 (s, 1H), 7.41–7.62 (m, 8H), 7.980 (s, 1H)

4-[ 3-(4-tert-butylaminocarbonylphenyl )-3-hydroxy-3-( 4-methoxyphenyl)propyl]-1H-imidazole ¹H NMR (as base, CDCl₃):
1.45 (s, 9H), 2.50–2.70 (m, 4H), 3.76 (s, 3H), 5.95 (br s, 1H), 6.71 (s, 1H), 6.82 (d, 2H), 7.26 (s, 1H), 7.37 (d, 2H), 7.52 (d, 2H), 7.62 (d, 2H)

b) 4-[3-(4-tert-butylaminocarbonylphenyl)- 3-phenyl-2-propenyl]-1H-imidazole

4-[3-(4-tert-butylaminocarbonylphenyl)- 3-hydroxy-3-phenylpropyl]-1H-imidazole (2,5 g, 6,6 mmol) is dissolved in methylene chloride (50 ml) and thionyl chloride (3,2 g, 26,9 mmol) is added to the solution. The mixture is refluxed for two hours. The solvents are evaporated. 2M sodium hydroxide is added to the residue and the product is extracted into ethyl acetate and dried. The product is convened to its HCl salt with dry hydrogen chloride gas and the solvent is evaporated. Yield 2,14 g, 91%.

¹H NMR (as HCl-salt, MeOH-d₄):
1.44 and 1.47 (2s, together 9H), 3.54 and 3.57 (2d, together 2H), 6.33 and 6.39 (2t, together 1H), 7.18–7.47 (m, 8H), 7.68 and 7.81 (2d, together 2H), 8.82 (d, 1H)

With the same dehydration procedure were also prepared the two following compounds:

4-[3-(4-tert-butylaminocarbonylphenyl )-3-( 4-fluorophenyl)-2-propenyl]-1H-imidazole ¹H NMR (as HCl-salt, MeOH-d₄):
1.44 and 1.47 (2s, together 9H), 3.53 and 3.56 (2d, together 2H), 6.29 and 6.38 (2t, together 1H), 7.03 (t, 1,25H=2H of the other isomer), 7.00–7.34 (m, together 5,75H=5H of both isomers and 2H of the other isomer), 7.68 and 7.81 (2d, together 2H), 8.81 (d, 1H)

1-benzyl-[3-(4-tert-butylaminocarbonylphenyl)- 3-(4-fluorophenyl)-2-propenyl]-1H-imidazole ¹H NMR (as base, CDCl₃):
1.46 and 1.50 (2s, together 9H), 3.23 and 3.26 (2d, together 2H), 4.96 and 5.29 (2s, together 2H), 5.96 and 6.01 (2 br s, together 1H), 6.03 and 6.11 (2l, together 1H), 6.88–7.27 (12H), 7.42–7.51 (2s, together 1H), 7.60 and 7.68 (2d, together 2H)

c) 4-[3-(4-tert-butylaminocarbonylphenyl)- 3-phenylpropyl]-1H-imidazole

4-[3-(4-tert-butylaminocarbonylphenyl)-3-phenyl-2-propenyl]-1H-imidazole hydrochloride is hydrogenated in ethanol using 10% Pd/C as a catalyst to give the product. Yield 95%.

¹H NMR (as HCl-salt, MeOH-d₄):
1.43 (s, 9H), 2.45–2.52 (dist q, 2H), 2.68 (dist t, 2H), 4.05

(t, 1H), 7.16–7.37 (m, 6H), 7.38 (d, 2H), 7.68 (d, 2H), 8.76 (d, 1H)

By the same method was also prepared 4-[3-( 4-tert-butylaminocarbonylphenyl)-3-(4-fluorophenyl)propyl]-1H-imidazole.

$^1$H NMR (as base, CDCl$_3$):
1.44 (s, 9H), 2.30–2.38 (dist q, 2H), 2.50 (dist t, 2H), 3.92 (t, 1H), 6.06 (br s, 1H), 6.69 (s, 1H), 6.92 (t, 2H), 7.12 (dd, 2H), 7.20 (d, 2H), 7.41 (s, 1H), 7.59 (d, 2H)

d) 4-[3-(4-cyanophenyl)-3-phenylpropyl]-1H-imidazole

4-[3-(4-tert-butylaminocarbonyl)-3-phenylpropyl]-1 H-imidazole is refluxed in thionylchloride for 2 hours. The solvent is evaporated and 2M sodium hydroxide is added. The product is extracted into ethyl acetate, dried and the solvent is evaporated. The product is purified by flash chromatography (CH$_2$Cl$_2$:MeOH 9:1).

4-[3-(4-cyanophenyl)-3-(4-fluorophenyl)propyl]-1H-imidazole is prepared by the same way from 4-[3-(4-tert-butylaminocarbonylphenyl)- 3-(4-fluorophenyl)propyl]-1H-imidazole.

EXAMPLE 3

4-[4,4-bis(4-cyanophenyl)butyl]-1H-imidazole a) 1-benzyl-5-[3,3-b is (4-tert-butylaminocarbonylpheny-3-hydroxypropyl]-1H-imidazole The title compound is prepared with the procedure described in the example 1a ) using ethyl (1-benzyl-5-imidazolyl)propionate (10 g, 39 mmol), n-butyl lithium (150 mmol) and 4-tert-butylaminocarbonylbromobenzene (18.8 g, 77 mmol) as starting materials.

$^1$H NMR (as base, CDCl$_3$):
1.45 (s, 18H), 2.40–2.50 (m, 4H), 4.95 (s, 2H), 6.30 (s, 2H), 6.79 (s, 1H), 6.92–6.95 (m, 2H), 7.28–7.30 (m, 3H), 7.36 (d, 4H), 7.46 (s, 1H), 7.60 (d, 4H) 1-benzyl-5-[4,4-bis(4-tert-butylaininocarbonylphenyl)- 4-hydroxy-butyl]-1H-imidazole is prepared in the same way using ethyl (1-benzyl-5-imidazolyl)butyrate as a starting material.

$^1$H NMR (as base, CDCl$_3$):
1.45 (s, 18H), 1.46–1.60 (m, 2H), 2.22–2.28 (m, 2H), 2.41 (t, 2H), 5.00 (s, 2H), 6.30 (s, 2H), 6.70 (s, 1H), 6.99–7.02 (m, 2H), 7.30–7.36 (m, 3H), 7.38 (d, 4H), 7.44 (s, 1H), 7.60 (d, 4H)

MS: 580 (14, M$^+$.), 91(100)

b) 1-benzyl-5-[4,4-bis(4-cyanophenyl)- 3-butenyl]-1H-imidazole 1-benzyl-5-[4,4-bis(4-tert-butylaminocarbonyl)- 4-hydroxybutyl]-1H-imidazole is heated in thionyl chloride following the precedure of the example 1b) to give the title compound. The same reaction can be done in boiling acetonitrile using 1,2 mol of PCl$_5$ as a reagent.

$^1$H NMR (as base, CDCl$_3$):
2.34 (q, 2H), 2.58 (t, 2H), 4.98 (s, 2H), 6.18 (t, 1H), 6.82 (s, 1H), 6.96–7.00 (m, 2H), 7.12 (d, 2H), 7.18 (d, 2H), 7.29–7.32 (m, 3H), 7.55 (d, 2H), under which (s, 1H), 7.66 (d, 2H)

c) 4-[4,4-bis(4-cyanophenyl)butyl]-1H-imidazole 1-benzyl-5-[4,4-bis(4-cyanophenyl)- 3-butenyl]-1H-imidazole hydrochloride is hydrogenated in ethanol using 10% Pd/C as a catalyst to give the product.

$^1$H NMR (as HCl-salt, MeOH-d$_4$):
1.60 (quintet, 2H), 2.18 (q, 2H), 2.77 (t, 2H), 4.19 (t, 1H), 7.27 (s, 1H), 7.47 (d, 4H), 7.67 (d, 4H), 8.74 (s, 1H)

MS: 326 (22, M$^+$.), 190(18), 96(100), 81(48)

EXAMPLE 4

4-[ 3,3-bis(4-cyanophenyl)propyl]-1H-imidazole a) 4-[3,3-bis(4-tert-butylaminocarbonyl)- 3-hydroxypropyl]-1H-imidazole The title compound is prepared from the corresponding benzyl protected compound (see example 3a) by hydrogen transfer reaction described in the example 2a).

$^1$H NMR (as base, CDCl$_3$):
1.44 (s, 18H), 2.45–2.60 (m, 4H), 6.13 (s, 2H), 6.58 (s, 1H), 7.36 (s, 1H), 7.46 (d, 4H), 7.58 (d, 4H)

b) 4-[3,3-bis(4-cyanophenyl)-2-propenyl]-1H-imidazole

4-[3,3-bis(4-tert-butylaminocarbonyphenyl)-3-hydroxypropyl]-1H-imidazole is heated in thionyl chloride following the procedure of the example 1b) to give the product.

$^1$H NMR (as HCl-salt, MeOH-d$_4$):
3.58 (d, 2H), 6.57 (t, 1H), 7.39–7.44 (m, 5H), 7.68 (d, 2H), 7.84 (d, 2H), (d, 2H) 8.84 (d, 1H)

c) 4-[3,3-bis(4-cyanophenyl)propyl]-1H-imidazole

4-[3,3-bis(4-cyanophenyl)-2-propenyl]-1H-imidazole hydrochloride is hydrogenated in ethanol using 10% Pd/C as a catalyst to give the product.

$^1$H NMR (as HCl-salt, MeOH-d$_4$):
2.49–2.56 (m, 2H), 2.69 (dist t, 2H), 4.24 (t, 1H), 7.31 (s, 1H), 7.53 (d, 4H), 7.69 (d, 4H), 8.78 (d, 1H)

EXAMPLE 5

4-[ 3-(4-cyanophenyl)-3-(4-trifluoromethylphenyl)propyl]- 1H-imidazole a) 4-[3-(4-cyanophenyl)-3-(4-trifiuoromethylphenyl)-2-propenyl]-1H-imidazole 4-[3-(4-tert-butylaminocarbonylphenyl)-3-(4-trifluoromethylphenyl)- 3-hydroxypropyl]-1H-imidazole is refluxed with PCl$_5$ (1,2 eqv) in dry acetonitrile to give the product. Yield 97%.

$^1$H NMR (as base, CDCl$_3$):
3.424 (d, 2H), 6.461 and 6.510 (2d, together 1H), 6.767 (s, 1H), 7.30–7.39 (m, 2H), 7.52–7.72 (m, 7H)

b) 4-[3-(4-cyanophenyl)-3-(4-trifluoromethylphenyl)propyl]-1H-imidazole

4-[3-(4-cyanophenyl)-3-(4-trifiuoromethylphenyl)-2-propenyl]-1H-imidazole is hydrogenated in ethanol using 10% Pd/C as a catalyst to give the product.

$^1$H NMR (as base, CDCl$_3$):
2.30–2.48 (m, 2H), 2.53–2.58 (m, 2H), 4.080 (t, 1H), 6.732 (s, 1H), 7.31–7.35 (m, 4H), 7.54–7.59 (m, 5H)

EXAMPLE 6

4-[3,3-bis(4-cyanophenyl)propyl]-1H-imidazole a) 1-benzyl-4-[3,3-bis(4-oxazolephenyl)-3-hydroxypropyl]-1H-imidazole 4,8 g (0,0187 mol) of 4-bromophenyloxazoline in minor volume of dry tetrahydrofuran is added dropwise to 0,9 g (0,0375 mol) of magnesium turnings with stirring under nitrogen atmosphere at room temperature. After the addition is complete the reaction mixture is stirred at room temperature for 2 hours. 2 g (0,0078 mol) of ethyl 3-(1-benzyl-1H-imidazol-4-yl)propionate in 10 ml of tetrahydrofuran is added dropwise with stirring to the slightly warmed reaction mixture. After the addition is complete the reaction mixture is refluxed for 4 hours. 10 ml of water is added to the reaction mixture to stop the reaction. The mixture is made acidic with hydrogen chloride and the product is precipitated as its hydrochloride salt. The precipitate is filtered and washed with water and ethyl acetate. Melting point of the product as base is 253°–255° C.

$^1$H NMR (as base, CDCl$_3$):

1.4 (s, 12H), 2.4 (s, 4H), 4.1 (s, 4H), 4.9 (s, 2H), 6.8 (s, 1H), 6.9 (dd, 2H) 7.3 (m, 3H), 7.3 (d, 4H), 7.4 (s, 1H), 7.8 (d, 4h)

b) 1-benzyl-4-[3,3-bis(4-cyanophenyl)-2-propenyl]-1H-imidazole 1 eqv. of 1-benzyl-4-[3,3-bis( 4-oxazolephenyl)propyl]-1H-imidazole is refluxed in 20 eqv. of thionyl chloride for 8 hours. Thionyl chloride is evaporated and the residue is silted up with toluene. Toluene is evaporated and water is added to the residue. The water solution is first washed with diethyl ether and then the product as HCl-salt is extracted into methylene chloride.

$^1$H NMR (as HCl-salt, MeOH-d$_4$):
3.4 (d, 2H), 5.3 (s, 2H), 6.4 (t, 1 H), 7.1 (m, 2H), 7.2 (d, 2H), 7.3 (d, 2H), 7.3 (m, 3H), 7.4 (s, 1H), 7.6 (d, 2H), 7.7 (d, 2H), 8.9 (s, 1H)

c) 4-[3,3-bis(4-cyanophenyl)propyl]-1H-imidazole 1 eqv. of 1-benzyl-4-[3,3-bis(4-cyanophenyl)-2-propenyl] -1H-imidazole hydrochloride is dissolved in ethanol (40 ml) and a catalytic aamount of 10% Pd/C is added. The reaction mixture is stirred at 40° C. in a hydrogen atmosphere until the uptake of hydrogen ceases. The mixture is filtered and the filtrate is evaporated to dryness. The residue which is the product is purified by column chromatography methylene chloride-methanol (9:1) as eluent.

$^1$H NMR (as base, CDCl$_3$):
2.4 (m, 2H), 2.5 (m, 2H), 6.7 (s, 1H), 7.3 (d, 4H), 7.6 (d, 4H), 7.6 (s, 1H)

EXAMPLE 7

4-[1 -(4-cyanophenyl)-4-phenylbutyl]-1H-imidazole a) 1-benzyl-5-(1-hydroxy-4-phenylbutyl)-1H-imidazole 6,03 g of magnesium turnings are covered with 60 ml of dry tetrahydrofuran. A solution of 1-bromo-3-phenylpropane (50,0 g) in 100 ml of dry tetrahydrofuran is then added dropwise to the mixture at such a rate that a smooth reaction is maintained. After the addition is complete, the reaction mixture is refluxed for one additional hour and cooled to room temperature. To the reaction mixture is then added dropwise the solution of 1-benzyl-5-imidazolecarbaldehyde (23,4 g) in 130 ml of tetrahydrofuran. After the addition is complete, the reaction mixture is refluxed for 2 hours, cooled and poured into cold water. Tetrahydrofuran is evaporated and conc. hydrochloric acid is added to the solution. The product is extracted into methylene chloride and evaporated to dryness.

$^1$H NMR (as base, CDCl$_3$):
1.5–1.9 (m, 4H), 2.56 (t, 2H), 4.48 (t, 1H), 5.15 and 5.25 (AB q, 2H), 6.89 (s, 1H), 7.05–7.35 (m, 10H), 7.40 (s, 1H)

The following compound was prepared by the same method from 1-bromo-3-(4-oxazolephenyl)propane and 1-benzyl-5-imidazolecarbaldehyde:

1-benzyl-5-[1-hydroxy-4-(4-oxazolephenyl)butyl]-1H-imidazole $^1$H NMR (as base, CDCl$_3$):
1.37 (s, 6H), 1.52–1.9 (m, 4H), 2.58 (t, 2H), 4.1 (s, 2H), 4.47 (t, 1H), 5.22 (2H), 6.94 (s, 1H), 7.03–7.1 (m, 2H), 7.15 (d, 2H), 7.25–7.4 (m, 3H), 7.47 (s, 1H), 7.84 (d, 2H)

b) 1-benzyl-5-(1-oxo-4-phenylbutyl)-1H-imidazole

The mixture of 27,5 g of 1-benzyl-5-(1-hydroxy-4-phenylbutyl)-1H-imidazole and 34,4 g of manganese dioxide in 550 ml of tetrachloroethylene is refluxed stirring for four hours. The reaction mixture is filtered and the filtrate is evaporated to dryness. The product is crystallized from ethyl acetate as hydrochloride salt.

$^1$H NMR (as HCl-salt, MeOH-d$_4$):
1.75–2.2 (m, 2H), 2.61 (t, 2H), 2.91 (t, 2H), 5.76 (s, 2H), 7.0–7.3 (m, 5H), 7.36 (s, 5H), 8.46 (s, 1H), 9.17 (s, 1H)

The following compound was prepared by the same method from 1-benzyl-5-[1-hydroxy-4-(4-oxazolephenyl) butyl]-1H-imidazole:

1 -benzyl-5-[4-(4-oxazolephenyl)-1-oxobutyl]-1H-imidazole $^1$H NMR (as base, CDCl$_3$):
1.38 (s, 6H), 1.99 (q, 2H), 2.64 (t, 2H), 2.76 (t, 2H), 4.09 (s, 2H), 5.53 (s, 2H), 7.14–7.18 (m, 3H), 7.22–7.35 (m, 4H), 7.63 (s, 1H), 7.74 (s, 1 H), 7.84 (d, 2H)

c) 1-benzyl-5-[1-hydroxy-4-phenyl-1-( 4-tert-butylaminocarbonylphenyl)butyl]-1H-imidazole 3,0 g of p-tert-butylaminocarbonylphenyl bromide is dissolved in 75 ml of dry tetrahydrofuran and cooled to −70° C. To the solution is added dropwise n-butyl lithium (1,8 g) in hexane and the mixture is stirred for 30 minutes. 1-benzyl-5-(1-oxo-4-phenylbutyl)-1H-imidazole (4,3 g) in 75 ml of tetrahydrofuran is added to the mixture at −70° C. and then the mixture is allowed to warm to room temperature and stirring is continued over night. Saturated ammonium chloride is added to the mixture and the solution is extracted with ethyl acetate. Ethyl acetate fractions are combined and evaporated to dryness.

$^1$H NMR (as base, CDCl$_3$):
1.25–1.35 (m, 1 H), 1.47 (s, 9H), 1.7–1.8 (m, 1 H), 2.21 (t, 2H), 2.55 (t, 2H), 4.67 and 4.79 (AB q, 2H), 6.79–6.82 (m, 2H), 7.0–7.3 (m, 12H), 7.57 (d, 2H)

The following compound was prepared by the same method from 1-benzyl-5-[4-(4-oxazolephenyl)-1-oxobutyl]-1H-imidazole and p-tert-butylaminocarbonylphenyl bromide:

1-benzyl-5-[1-(4-tert-butylaminocarbonylphenyl)-1-hydroxy4-(4-oxazolephenyl)butyl]-1H-imidazole $^1$H NMR (as base, CDCl$_3$):
1.36 (s, 6H), 1.47 (s, 9H), 1.65–1.9 (m, 2H), 2.14–2.22 (m, 2H), 2.57 (t, 2H), 4.07 (s, 2H), 4.7 (AB q, 2H), 6.76–6.8 (m, 2H), 7.0–7.35 (m, 9H), 7.6 (d, 2H), 7.8 (d, 2H)

d) 1-benzyl-5-[1-(4-cyanophenyl)-4-phenyl-1-butenyl]-1H-imidazole 1,95 g of 1-benzyl-5-[1-hydroxy-4-phenyl- 1-(4-tert-butylaminocarbonylphenyl)butyl]-1H-imidazole is refluxed 2 hours in 40 ml of thionyl chloride.

Thionyl chloride is evaporated and the residue is dissolved in ethyl acetate and washed with 5% sodium hydrogen carbonate solution and with water. Ethyl acetate is evaporated and the residue is purified by flash chromatography.

$^1$H NMR (as HCl-salt, MeOH-d$_4$):
2.55 (q, 2H), 2.76 (t, 2H), 5.01 (s, 2H), 6.26 (t, 1H), 6.88–7.34 (m, 12H), 7.54 (s, 1H), 7.59 (d, 2H), 8.98 (s, 1H)

e) 4-[1-(4-cyanophenyl)-4-phenylbutyl]-1H-imidazole 1-benzyl-5-[1-(4-cyanophenyl)-4-phenyl-1-butenyl]-1H-imidazole hydrochloride (1,77 g) is dissolved in ethanol and a catalytic amount of 10% Pd/C is added. The reaction mixture is agitated vigorously at room temperature in hydrogen atmosphere until the reduction of the double bond and the debenzylation are complete. The reaction mixture is filtered and evaporated to dryness. The product is purified by flash chromatography.

$^1$H NMR (as HCl-salt, MeOH-d$_4$):
1.5–1.65 (m, 2H), 1.95–2.15 (m, 2H), 2.65 (distorted t, 2H), 4.21 (t, 1H), 7.14–7.26 (m, 5H), 7.42 (d, 2H), 7.43 (s, 1H), 7.71 (d, 2H), 8.79 (s, 1H)

EXAMPLE 8

4-[1-(4-cyanophenyl )-4-(4-fluorophenyl)butyl]-1H-imidazole a) 1-benzyl-5-[4-(4-fluorophenyl)-1-hydroxybutyl]-1H-imidazole 1-benzyl-5-[4-(4-fluorophenyl)-1-hydroxybutyl]-1H-imidazole is prepared from 1-bromo-3-(4-fluorophenyl)propane and 1-benzyl-5-imidazole carbaldehyde by the same method described in example 7a).

$^1$H NMR (as base, CDCl$_3$):
1.5–1.75 (m, 2H), 1.76–1.84 (m, 2H), 2.53 (t, 2H), 4.49 (t, 1 H), 5.20 and 5.26 (AB q, 2H), 6.91–7.1 (m, 7H), 7.30–7.35 (m, 3H), 7.48 (s, 1H)

b) 1-benzyl-5-[4-(4-fluorophenyl)-1-oxobutyl]-1H-imidazole 1-benzyl-5-[4-(4-fluorophenyl)-1-oxobutyl]-1H-imidazole is prepared from 1-benzyl-5-[4-(4-fluorophenyl)-1-hydroxybutyl]-1H-imidazole by the same method described in example 7b).

$^1$H NMR (as base, CDCl$_3$):
1.9–2.0 (m, 2H), 2.58 (t, 2H), 2.76 (t, 2H), 5.52 (s, 2H), 6.9–7.32 (m, 9H), 7.63 (s, 1H), 7.75 (s, 1H)

c) 1-benzyl-5-[4-(4-fluorophenyl)-1-hydroxy-1-( 4-tert-butylaminocarbonylphenyl)butyl]-1H-imidazole 1-benzyl-5-[4-(4-fluorophenyl)-1-hydroxy-1-(4-tert-butylaminocarbonylphenyl)butyl]-1H-imidazole is prepared from 1-benzyl-5-[4-(4-fluorophenyl)-1-oxobutyl]-1H-imidazole by the same method described in example 7c).

$^1$H NMR (as base, CDCl$_3$+MeOH-d$_4$):
1.15–1.35 (m, 1 H), 1.47 (s, 9H), 1.6–1.8 (m, 1 H), 2.15–2.25 (m, 2H), 2.52 (t, 2H), 4.74 and 4.80 (AB q, 2H), 6.80–7.31 (m, 13H), 7.57 (d, 2H)

d) 4-[4-(4-fluorophenyl)-1-hydroxy-1-(4-tert-butylaminocarbonylphenyl)butyl]-1H-imidazole 12,95 g of 1-benzyl-5-[4-( 4-fluorophenyl)-1-hydroxy-1-(4-tert-butylaminocarbonylphenyl)butyl]-1-H-imidazole is dissolved into ethanol (400 ml) and water (130 ml). 8,17 g of ammonium formate and 1,3 g of 10% Pd/C is added to the solution and the mixture is refluxed for three hours. Then the reaction mixture is filtered through siliceous earth and the flitrate is evaporated to dryness. The residue is dissolved into ethyl acetate, washed with 2M aqueous sodium hydroxide and water, dried and evaporated to dryness.

$^1$H NMR (as base, CDCl$_3$):
1.3–1.5 (m, 1 H), 1.47 (s, 9H), 1.6–1.8 (m, 1 H), 2.0–2.3 (m, 2H), 2.45–2.60 (m, 2H), 6.78 (s, 1 H), 6.91 (t, 2H), 6.94–7.07 (m, 2H), 7.43 (d, 2H), 7.50 (s, 1 H), 7.61 (d, 2H)

e) 4-[1-(4-cyanophenyl)-4-(4-fluorophenyl)-1-butenyl]-1H-imidazole 15,0 g of 4-[4-(4-fluorophenyl)-1-hydroxy-1-(4-tert-butylaminocarbonylphenyl)butyl]-1H-imidazole is dissolved into dry acetonitrile (450 ml). 15,4 g of phosphorus pentachloride is added and the mixture is refluxed for five hours. Then the mixture is poured to water and acetonitrile is evaporated. The water solution is rendered alkaline and extracted with ethyl acetate. The ethyl acetate phase is washed with water, dried and evaporated to dryness.

$^1$H NMR (as base, CDCl$_3$):
2.28 (q, 2H), 2.69 (t, 2H), 6.04 and 6.45 (2t, 1H), 6.36 and 6.85 (2s, 1H), 6.89–7.64 (m, 9H)

The following compound was prepared by the same method from 4-[3-(4-tert-butylaminocarbonylphenyl)-3-hydroxy-3-(4-methoxyphenyl)propyl ]-1 H-imidazole:

4-[3-(4-cyanophenyl)-3-(4-methoxyphenyl)prop-2-en-1-yl]- 1H-imidazole $^1$H NMR (as base, CDCl$_3$):
3.38 and 3.48 (2d, together 2H), 3.79 and 3.84 (2s, together 3H), 6.25 and 6.35 (2H, together 1H), 6.78 (s, 1H), 6.81 and 6.92 (2d, together 2H), 7.09 and 7.11 (2d, together 2H), 7.32 and 7.35 (2d, together 2H), 7.52 and 7.65 (2d, together 2H), 7.66 (s, 1H)

f) 4-[1-(4-cyanophenyl)-4-(4-fluomphenyl)butyl]-1H-imidazole

4-[1-(4-cyanophenyl)-4-(4-fluorophenyl)butyl]- 1H-imidazole is prepared from -4-[1-( 4-cyanophenyl)-4-(4-fluorophenyl)-1-butenyl]-1H-imidazole by the method described in example 7e). Yield 80%.

$^1$H NMR (as base, CDCl$_3$):
1.4–1.65 (m, 2H), 1.87–1.96 (m, 1 H), 2.1–2.2 (m, 1 H), 2.58 (t, 2H), 3.95 (t, 1H), 6.72 (s, 1H), 6.92 (t, 2H), 7.02–7.07 (m, 2H), 7.32 (d, 2H), 7.49 (s, 2H), 7.53 (d, 2H)

The following compound was prepared by the same method from 4-[3-(4-cyanophenyl)-3-(4-methoxyphenyl)prop-2-en-1-yl]-1H-imidazole:

4-[3-(4-cyanophenyl)-3-(4-methoxyphenyl)propyl]-1H-imidazole $^1$H NMR (as HCl-salt, MeOH-d$_4$):
2.43–2.49 (m, 2H), 2.65–2.70 (m, 2H), 3.75 (s, 3H), 4.04 (t, 1H), 6.87 (d, 2H), 7.21 (d, 2H), 7.29 (s, 1H), 7.48 (d, 2H), 7.65 (d, 2H), 8.77 (s, 1H)

EXAMPLE 9

4-[1-(4-cyanophenyl)4-(4-fluorophenyl)butyl]-1 H-imidazole a) 4-[4-(4-fluorophenyl)-1-(4-tert-butylaminocarbonylphenyl)butyl]-1H-imidazole 1-benzyl-5-[4-(4-fluorophenyl)-1-hydroxy- 1-(4-tert-butylaminocarbonylphenyl)butyl]-1H-imidazole (10 g) is dissolved into acetic acid (100 ml). Ammonium formate (6,3 g) and 10% Pd/C (1 g) is added to the solution and the mixture is refluxed for three hours. After the reaction is completed the mixture is filtered through siliceous earth and the flitrate is evaporated to dryness. The residue is dissolved into ethyl acetate, washed with 2M aqueous sodium hydroxide and water, dried and evaporated to dryness. Yield 92%.

$^1$H NMR (as base, CDCl$_3$):
1.46 (s, 9H), 1.4–1.63 (m, 2H), 1.8–2.0 (m, 1H), 2.1–2.25 (m, 1H), 2.5–2.65 (m, 2H), 3.95 (t, 1H), 6.72 (s, 1H), 6.9–6.95 (m, 2H), 7.02–7.07 (m, 2H), 7.26 (d, 2H), 7.55 (s, 1H), 7.61 (d, 2H)

b) 4-[1-(4-cyanophenyl)-4-(4-fluorophenyl)butyl]-1H-imidazole

4-[4-(4-fluorophenyl)-1-(4-tert-butylaminocarbonylphenyl)butyl]-1H-imidazole (7 g) is dissolved into dry acetonitrile (200 ml). 3,6 g of phosphorus pentachloride is added and the mixture is poured into water and acetonitrile is evaporated. The water solution is rendered alkaline and extracted with ethyl acetate. The ethyl acetate phase is washed with water, dried and evaporated to dryness. Yield 85%.

EXAMPLE 10

4-[1-(4-cyanophenyl)-4-(4-fluorophenyl)- 1-butenyl]-1H-imidazole, isomers a and b a) 1-benzyl-5-[4-(4-fluorophenyl)-1-hydroxybutyl]-1H-imidazole 5,4 g of magnesium turnings are covered with 50 ml of dry tetrahydrofuran. A solution of 1-bromo-3-(4-fluorophenyl)propane (48,7 g) in 200 ml of dry tetrahydrofuran is then added dropwise to the mixture at such a rate that a smooth reaction is maintained. After the addition is complete, the reaction mixture is refluxed for one additional hour and cooled to room temperature. To the reaction mixture is then added dropwise the solution of 1-benzyl-5-imidazolecarbaldehyde (20,9 g) in 200 ml of tetrahydrofuran. After the addition is complete, the reaction mixture is refluxed for 2 hours, cooled and poured into cold saturated ammonium chloride solution. Tetrahydrofuran phase is removed and the water phase is extracted three times with ethyl acetate. Organic phases are combined, dried and evaporated to dryness. The residue is suspended with diethyl ether and filtered. Yield 86%.

$^1$H NMR (as base, CDCl$_3$):
1.5–1.75 (m, 2H), 1.76–1.84 (m, 2H), 2.53 (t, 2H), 4.49 (t, 1H), 5.20 and 5.26 (AB q, 2H), 6.91–7.1 (m, 7H), 7.30–7.35 (m, 3H), 7.48 (s, 1H)

b) 1-benzyl-5-[4-(4-fluorophenyl)-1-oxobutyl]-1H-imidazole

The mixture of 36,1 g of 1-benzyl-5-(4-(4-fluorophenyl)-1-hydroxybutyl]-1H-imidazole and 53 g manganese dioxide in 550 ml of tetrachloroethylene is refluxed stirring for four hours. The reaction mixture is filtered through siliceous earth and the flitrate is evaporated to dryness. The product is crystallized from acetone as hydrochloride salt.

$^1$H NMR (as base, CDCl$_3$):
1.9–2.0 (m, 2H), 2.58 (t, 2H), 2.76 (t, 2H), 5.52 (s, 2H), 6.9–7.32 (m, 9H), 7.63 (s, 1H), 7.75 (s, 1H)

c) 1-benzyl-5-[4-(4-fluorophenyl)-1-hydroxy-1-(4-tert-butylaminocarbonylphenyl)butyl]-1H-imidazole 9,9 g of p-tert-butylaminocarbonylphenyl bromide is dissolved in 200 ml of dry tetrahydrofuran and cooled to −70° C. To the solution is added dropwise n-butyl lithium (5,3 g) in hexane and the mixture is stirred for one hour. 1-benzyl-5-[4-(4-fluorophenyl)-1-oxobutyl]-1H-imidazole (10,4 g) in 200 ml of tetrahydrofuran is added to the mixture at −70° C. and the mixture is allowed to warm to room temperature and stirring is continued over night. Saturated ammonium chloride is added to the mixture and the solution is extracted with ethyl acetate. Ethyl acetate fractions are combined and evaporated to dryness.

$^1$H NMR (as base, CDCl$_3$+MeOH-d$_4$):
1.15–1.35 (m, 1H), 1.47 (s, 9H), 1.6–1.8 (m, 1H), 2.15–2.25 (m, 2H), 2.52 (t, 2H), 4.74 and 4.80 (AB q, 2H), 6.80–7.31 (m, 13H), 7.57 (d, 2H)

d) 4-[4-(4-fluorophenyl)-1-hydroxy-1-(4-tert-butylaminocarbonylphenyl)butyl]-1H-imidazole 1-benzyl-5-[4-(4-fluorophenyl)-1-hydroxy-1-(4-tert-butylaminocarbonylphenyl)butyl]-1H-imidazole hydrochloride (12,95 g) is dissolved into aqueous ethanol (400 ml) and 1,3 g of 10% Pd/C is added. Ammonium formate (8,17 g) is added to the boiling solution in small portions. The mixture is refluxed for three hours. Then the reaction mixture is filtered through siliceous earth and the filtrate is evaporated to dryness. The residue is dissolved to methylene chloride, washed with 2M sodiumhydroxide and water, dried and evaporated to dryness. Yield 79%.

$^1$H NMR (as base, CDCl$_3$):
1.3–1.5 (m, 1H), 1.47 (s, 9H), 1.6–1.8 (m, 1H), 2.0–2.3 (m, 2H), 2.45–2.5 (m, 2H), 6.78 (s, 1H), 6.91 (t, 2H), 6.94–7.07 (m, 2H), 7.43 (d, 2H), 7.50 H), 7.61 (d, 2H)

e) 4-[1-(4-cyanophenyl)-4-(4-fluorophenyl)-1-butenyl]-1H-imidazole, isomers a and b 4-[4-(4-fluorophenyl)-1-hydroxy-1-(4-tert-butylaminocarbonylphenyl)butyl]-1H-imidazole (7,6 g) is dissolved into thionyl chloride (75 ml) and refluxed for two hours. Thionyl chloride is evaporated and the residue is dissolved to ethyl acetate, washed with 2M sodium hydroxide solution and water, dried and evaporated to dryness. The residue is crystallized from ethyl acetate as hydrogen chloride salt (isomer a). The mother liquid is washed with 2 M sodium hydroxide solution and water, dried and concentrated. Diethyl ether is added to the solution and the precipitated product is filtered (isomer b). Yields 53% isomer a and 17% isomer b.

$^1$H NMR (as HCl-salt, MeOH-d$_4$):
Isomer a: 2.4 (q, 2H), 2.77 (t, 2H), 6.47 (t, 1H), 6.92–7.00 (m, 2H), 7.03 (s, 1H), 7.08–7.13 (m, 3H), 7.21–7.24 (m, 2H), 7.76–7.78 (m, 2H), 8.87 (d, 1H)
Isomer b: 2.61 (q, 2H), 2.85 (t, 2H), 6.61 (t, 1H), 6.96–7.01 (m, 2H), 7.16–7.21 (m, 3H), 7.34 (d, 1H), 7.4 (d, 2H), 7.71 (d, 2H), 8.93 (d, 1H)

EXAMPLE 11

4-[1-(4-cyanophenyl)-3-(4-fluorophenyl)-1-propenyl]-1H-imidazole a) 1-benzyl-5-[1-(4-tert-butylaminocarbonylphenyl)-3-(4-fluorophenyl)-1-hydroxypropyl]-1H-imidazole 1-benzyl-5-[1-(4-tert-butylaminocarbonylphenyl)-3-(4-fluorophenyl)-1-hydroxypropyl]-1H-imidazole is prepared from 1-benzyl-5-[3-(4-fluorophenyl)-1-oxopropyl]-1H-imidazole (synthesized by aldol condensation from 1-benzyl-5-acetyl-1H-imidazole and 4-fluorobenzaldehyde followed by hydrogenation) by the method described in example 7c).

$^1$btH NMR (as HCl-salt, MeOH-d$_4$):
1.46 (s, 9H), 2.08–2.19 (m, 1H), 2.55–2.60 (m, 2H), 2.79–2.89 (m, 1H), 5.06 (d, 1H), 5.35 (d, 1H), 6.91–6.98 (m, 4H), 7.07–7.12 (m, 2H), 7.22–7.28 (m, 3H), 7.53 (d, 2H), 7.74 (d, 2H), 7.87 (d, 1H), 8.69 (d, 1H)

b) 4-[1-(4-tert-butylaminocarbonylphenyl)-3-(4-fluorophenyl) 1-hydroxypropyl]-1H-imidazole 4-[1-(4-tert-butylaminocarbonylphenyl)-3-(4-fluorophenyl)-1-hydroxypropyl]-1H-imidazole is prepand from 1-benzyl-5-[1-(4-tert-butylamino-carbonylphenyl)-3-(4-fluorophenyl)-1-hydroxypropyl]-1H-imidazole by the method described in example 7d).

$^1$H NMR (as base, CDCl$_3$):
1.46 (s, 9H), 2.26–2.42 (m, 2H), 2.44–2.58 (m, 1H), 2.63–2.76 (m, 1H), 6.3 (brs, 1H), 6.86 (s, 1H), 6.91 (t, 2H), 7.04–7.09 (m, 2H), 7.51 (s, 1H), 7.52 (d, 2H), 7.65 (d, 2H)

c) 4-[1-(4-cyanophenyl)-3-(4-fluorophenyl)-1-propenyl]-1H-imidazole, isomers a and b 4-[1-(4-cyanophenyl)-3-(4-fluorophenyl)-1-propenyl]-1H-imidazole is prepared from 4-[1-(4-tert-butylaminocarbonylphenyl)-1-hydroxypropyl]-1H-imidazole by the method described in example 8e). Yield was 96,5%. The product contains isomers a and b in the ratio 4:1. The isomer a is precipitated as a hydrochloride salt from ethyl acetate. The filtrate is washed with 2M sodium hydroxide. The isomer b is precipitated from concentrated ethyl acetate solution as a base.

$^1$H NMR, isomer a (as HCl-salt, MeOH-d$_4$):
3.45 (d, 2H), 6.26 (t, 1H), 7.02 (t, 2H), 12 (d, 1H), 7.18 (dd, 2H), 7.55 (d, 2H), 7.88 (d, 2H), 8.91 (d, 1H)

$^1$H NMR, isomer b (as HCl-salt, MeOH-d$_4$):
3.64 (d, 2H), 6.75 (t, 1H), 7.05 (t, 2H), 7.23 (dd, 2H), 7.48 (d, 2h), 7.73 (d, 2H), 7.73 (d, 1H), 9.03 (d, 1H)

EXAMPLE 12

4-[3-(4-cyanophenyl)-1-(4-fluorophenyl)-1-propenyl]-1H-imidazole a) 1-benzyl-5-[3-(4-tert-butylaminocarbonylphenyl)-1-(4-fluorophenyl)-1-hydroxypropyl]-1H-imidazole 1-benzyl-5-[3-(4-tert-butylaminocarbonylaminophenyl)-1-(4-fluorophenyl)1-hydroxypropyl]-1H-imidazole is prepared from 1-benzyl-5-[3-(4-tert-butylaminocarbonylphenyl)-1-oxopropyl]-1H-imidazole (synthesized by aldol condensation from 1-benzyl-5-acetyl-1H-imidazole and 4-ethoxycarbonylbenzaldehyde followed by hydrogenation, converting to corresponding acid chloride and allowing the product to react with tert-butylamine) and 4-bromofluorobenzene by the method described in the example 7c).

$^1$H NMR (as base, CDCl$_3$ +MeOH-d$_4$):
1.46 (s, 9H), 2.25 (dt, 1H), 2.45 (d quintet, 2H), 2.84 (dt, 1H), 4.77 and 4.98 (2d, AB pattern, 2H), 6.84–6.87 (m, 2H), 6.97 (t, 2H), 7.11 (d, 2h), 7.15 (s, 1H), 7.22–7.26 (m, 4H), 7.32 (dd, 2H), 7.58 (d, 2H)

b) 4-[3-(4-tert-butylaminocarbonylphenyl)-1-(4-fluorophenyl)-1-hydroxypropyl]-1H-imidazole 4-[3-(4-tert-butylaminocarbonylphenyl)-1-(4-fluorophenyl)-1-hydroxypropyl]-1H-imidazole is prepared from 1-benzyl-5-[3-( 4-tert-butylaminocarbonylphenyl)-1-(4-fluorophenyl)-1-hydroxypropyl]-1H-imidazole by the method described in example 8d).

$^1$H NMR (as base, CDCl$_3$+MeOH-d$_4$):
1.45 (s, 9H), 2.30–2.62 (m, 3H), 2.70–2.84 (m, 1 H), 6.28 (br s, 1H), 6.91 (br s, 1H), 7.03 (t, 2h), 7.18 (d, 2H), 7.46 (dd, 2H), 7.59 (d, 2H), 7.75 (br s, 1H)

c) 4-[3-(4-cyanophenyl)-1-(4-fluorophenyl)-1-propenyl]-1H-imidazole, isomers a and b 4-[3-(4-cyanophenyl)-1-(4-fluorophenyl)-1-propenyl]-1H-imidazole is prepared from 4-[3-(4-tert-butylaminocarbonylphenyl)-1-(4-fluorophenyl)-1-hydroxypropyl]-1H-imidazole by the method described in example 8e).

$^1$H NMR (as HCl-salt, MeOH-d$_4$):
3.56 and 3.72 (2d, together 2H), 6.54 and 6.55 (2t, together 1H), 7.12 and 7.25 (2t, together 2H), 7.30–7.44 (m, 4H), 7.67 and 7.69 (2d, together 2H), 7.11 and 7.70 (2s, together 1H), 8.91 and 9.00 (2s, together 1H)

EXAMPLE 13

4-[1,4-bis(4-cyanophenyl)butyl]-1H-imidazole a) 1-benzyl-5-[1-hydroxy-4-(4-oxazolephenyl)butyl]-1H-imidazole 0,73 g of magnesium turnings are covered with 30 ml of dry tetrahydrofuran. A solution of 1-bromo-3-(4-oxazole-phenyl)propane (9,1 g) in 70 ml of dry tetrahydrofuran is then added dropwise to the mixture at such a rate that a smooth reaction is maintained. After the addition is complete, the reaction is refluxed for half an hour and cooled to about 40° C. To the reaction mixture is then added dropwise the solution of 1-benzyl-5-imidazolecarbaldehyde (2,3 g) in 50 ml of tetrahydrofuran. After the addition is complete, the reaction mixture is refluxed for 2 hours, cooled and poured into saturated aqueous ammonium chloride solution. The phases are separated, THF-solution is dried and evaporated to dryness. The residue is triturated with petroleum ether, decanted and triturated again with petroleum ether and acetone. Precipitated product is filtered. Yield 76%.

$^1$H NMR (as base, CDCl$_3$):
1.37 (s, 6H), 1.52–1.9 (m, 4H), 2.58 (t, 2H), 4.1 (s, 2H), 4.47 (t, 1 H), 5.22 (q, 2H), 6.94 (s, 1 H), 7.03–7.1 (m, 2H), 7.15 (d, 2H), 7.25–7.4 (m,3H), 7.47 (s, 1H), 7.84 (d, 2H)

b) 1-benzyl-5-[4-(4-oxazolephenyl)-1-oxobutyl]-1H-imidazole

The mixture of 11,37 g of 1-benzyl-5-[1-hydroxy-4-(4-oxazolephenyl)butyl]-1Himidazole and 11 g of manganese dioxide in 180 ml of tetrachloroethylene is refluxed stirring for four hours. The reaction mixture is filtered through siliceous earth and the filtrate is evaporated to dryness. The product is crystallized from ethyl acetate as hydrochloride salt. Yield 81%.

$^1$H NMR (as base, CDCl$_3$):
1.38 (s, 6H, 1.99 (quintet, 2H), 2.64 (t, 2H), 2.76 (t, 2H), 4.09 (s, 2H), 5.53 (s, 2H), 7.14–7.18 (m, 3H), 7.22–7.35 (m, 4H), 7.63 (s, 1H), 7.74 (s, 1H), 7.8 (d, 2H)

c) 1-benzyl-5-[1,4-bis(4-oxazolephenyl)-1-hydroxybutyl]-1H-imidazole 0,93 g of magnesium turnings are covered with 30 ml of dry tetrahydrofuran. A solution of 1-bromo-3-(4-oxazole-phenyl)propane (9,88 g) in 70 ml of dry tetrahydrofuran is then added dropwise to the mixture at such a rate that a smooth reaction is maintained. After the addition is complete, the reaction mixture is refluxed for half an hour and cooled to about 40° C. To the reaction mixture is then added dropwise a solution of 1-benzyl-5-[4-(4-oxazole-phenyl)-1-oxobutyl]- 1H-imidazole (7,8 g) in 50 ml of tetrahydrofuran. After the addition is complete, the reaction mixture is refluxed for 2 hours, cooled and poured into saturated aqueous ammonium chloride solution. The phases are separated, THF-solution is dried and evaporated to dryness. The residue is triturated with ethyl acetate and filtered.

$^1$H NMR (as base, CDCl$_3$):
1.28–1.4 (m, 1H), 1.35 (s, 6H), 1.39 (s, 1H), 1.75–1.9 (m, 1H), 2.19 (distort t, 2H), 2.57 (t, 2H), 4.07 (s, 2H), 4.10 (s, 2H), 4.7 (AB q, 2H), 6.8–6.83 (m, 2H 7.07 (s, 1 H), 7.09 (d, 2H), 7.17–7.2 (m, 4H), 7.31 (d, 2H), 7.78 (d, 2H), 7.82 (d, 2H)

d) 4-[1,4-bis(4-oxazolephenyl)-1-hydroxybutyl]-1H-imidazole 1-benzyl-5-[1,4-bis(4-oxazolephenyl)-1-hydroxybutyl]-1H-imidazole (5,7 g) is dissolved into aqueous ethanol (100 ml) and 0,6 g of 10% Pd/C is added. Ammonium formate (3,1 g) is added to the boiling solution in small portions. The mixture is refluxed for 6 hours. Then the reaction mixture is filtered through siliceous earth and the filtrate is evaporated to dryness. The residue is dissolved to ethyl acetate, washed with 2M sodium hydroxide and water, dried and rendered acidic with hydrogen chloride gas. The ethyl acetate solution is concentrated and the precipitated product is filtered. Yield 92%.

$^1$H NMR (as HCl-salt, MeOH-d$_4$):
1.35–1.5 (m, 1 H), 1.65 (s, 6H), 1.66 (s, 6H), 1.7–1.9 (m, 1 H), 2.35–2.5 (m, 2H), 2.7–2.9 (m, 2H), 7.47 (d, 2H), 7.68 (d, 1 H), 7.83 (d, 2H), 8.12 (d, 8.01 (d, 2H), 2H), H), 8.85 (s, 1H)

e) 4-[1,4-bis(4-carboxyphenyl)-1-butenyl]-1H-imidazole
4-[1,4-bis(4-oxazolephenyl)-1-hydroxybutyl]-1H-imidazole (5,7 g) is refluxed with 6N aqueous hydrogen chloride (80 ml) for 4 hours. Cooled reaction mixture is filtered and the precipitate is washed with water. Yield 96%. Isomer ratio 85:15 (a:b).

$^1$H NMR (as HCl-salt, DMSO-d$_6$):
2.36 and 2.55 (q, 2H), 2.80 and 2.90 (t, 2H), 6.59 and 6.69 (t, 1H), 7.06 (s, 1H), 7.2 (d, 2H), 7.28 (d, 2H), 7.84 (d, 2H), 7.96 (d, 2H), 9.17 (s, 1H)

f) 4-[1,4-bis(4-cyanophenyl)-1-butenyl]-1H-imidazole
4-[1,4-bis(carboxyphenyl)-1-butenyl]-1H-imidazole hydrochloride (0,5 g) and carbonyldiimidazole (0,81 g) is stirred in dry dimethylformamide (2 ml) at room temperature for two hours. Ammonia gas is leaded to the reaction mixture and stirring is continued for half an hour. The product is precipitated as an oil by adding diethyl ether (60 ml) to the reaction mixture. Solvents are decanted and the residue is triturated with ethyl ether (20 ml), decanted and evaporated for moving the traces of ether. The residue is dissolved into dry acetonitrile (20 ml), phosphorus pentachloride (0,43 g) is added and the mixture is refluxed for an hour. Then the mixture is evaporated to dryness, water is added and the solution is rendered alkaline and extracted with ethyl acetate. Ethyl acetate phase is washed with water, dried and evaporated to dryness. The residue is purified by flash chromatography. Yield 65%. Isomer raio 88:12 (a:b).

$^1$H NMR (as base, CDCl$_3$):

2.34 (q, 2H), 2.78 (t, 2H), 5.97 and 6.51 (t, 1H), 6.40 and 6.87 (s, 1H), 7.18 (d, 4H), 7.52 (d, 2H), 7.64 (s, 1H), 7.64 (d, 2H)

We claim:

1. A compound which is a substituted imidazole of the formula (Ia)

a stereoisomer or a non-toxic pharmaceutically acceptable acid addition salt thereof wherein R$_1$ is CN, R$_2$ is H, CH$_3$, OCH$_3$, NO$_2$, NH$_2$, CF$_3$ CHF$_2$, Ch$_2$F or halogen; R' is H or $-CH_2-$⟨phenyl⟩$-R_3$ where R$_3$ is H, CH$_3$ or halogen; R$_4$ is H and R$_5$ is H or R$_4$ and R$_5$ together form a bond and n is 1 or 2.

2. A compound according to claim 1 wherein R$_4$ and R$_5$ are each H.

3. A compound according to claim 2 wherein R$_1$ and R$_2$ are in the para position of the respective phenyl group.

4. A compound according to claim 1 wherein R$_4$ and R$_5$ together form a bond.

5. A compound according to claim 4 wherein R$_1$ and R$_2$ are in the para position of the respective phenyl group.

6. A compound according to claim 1 wherein R' is H.

7. A compound according to claim 4 in the form of a stereoisomer or a non-toxic pharmaceutically acceptable acid addition salt.

8. A compound according to claim 1, which is 4-[3-(4-cyanophenyl)-3-phenylpropyl]-1H-imidazole, 4-[3-(4-cyanophenyl)- 3-(4fluorophenyl)propyl]-1H-imidazole, 4-[3-(4-cyanophenyl) -3-( 4-fluorophenyl)-2-propenyl]-1H-imidazole or a stereoisomer thereof, 4-[3-(4-cyanophenyl)-3-( 4-trifluoromethylphenyl)propyl- 1H-imidazole, 4-[3-(4-cyanophenyl)-3-( 4-methoxyphenyl)propyl]-1H-imidazole, or a non-toxic pharmaceutically acceptable acid addition salt thereof.

9. A method of inhibiting aromatase comprising administering to a subject in which such inhibition is desired, an aamount of a compound as claimed in claim 1 to produce the desired inhibition.

10. A pharmaceutical composition comprising an aromatase inhibiting aamount of a compound as claimed in claim 1 and a pharmaceutically acceptable carrier.

11. A method of inhibiting aromatase comprising administering to a subject in which such inhibition is desired, an amount of a composition as claimed in claim 10.

12. A compound which is a substituted imidazole of the formula (Ib)

a stereoisomer or a non-toxic pharmaceutically acceptable acid addition salt thereof wherein R$_1$ is CN and R$_2$ is H, CH$_3$, OCH$_3$ NO$_2$, NH$_2$, CF$_3$, CHF$_2$, CH$_2$F or halogen; R' is H or $-CH_2-$⟨phenyl⟩$-R_3$ where R$_3$ is H, CH$_3$ or halogen; R$_4$ is H and R$_5$ is H or R$_4$ and R$_5$ together form a bond and y is 0, 1 or 2.

13. A compound according to claim 12 wherein y is 1 or 2.

14. A compound according to claim 13 wherein R$_4$ and R$_5$ are each H.

15. A compound according to claim 14 wherein R$_1$ and R$_2$ are each in the para position of the respective phenyl group.

16. A compound according to claim 13 wherein R$_4$ and R$_5$ together form a bond.

17. A compound according to claim 16 wherein R$_1$ and R$_2$ are each in the para position of the respective phenyl group.

18. A compound according to claim 17 wherein R$_1$ is CN.

19. A compound according to claim 16 which is in the form of a stereoisomer or a non-toxic pharmaceutically acceptable acid addition salt.

20. A compound according to claim 13 wherein R' is H.

21. A compound according to claim 12, which is 4-[1-( 4-cyanophenyl)-4-phenylbutyl]-1H-imidazole, 4-[1-(4-cyanophenyl)-4-(4-fluorophenyl)butyl]- 1H-imidazole, 4-[1-(4-cyanophenyl)- 4-(4-fluorophenyl)-1-butenyl]-1H-imidazole, 4-[1-(4-cyanophenyl)-4-( 4-fluorophenyl)-1-butenyl]-1H-imidazole isomer a, 4-[1-( 4-cyanophenyl)-4-(4-fluorophenyl)-1-butenyl]-1-H-imidazole isomer b, 4-[1-(4-cyanophenyl)-3-(4-fluorophenyl)-1-propenyl]-1H-imidazole, 4-[1-(4-cyanophenyl)-3-(4-fluorophenyl)-1-propenyl]-1H-imidazole isomer a, 4-[(1-(4-cyanophenyl)-3-(4-fluorophenyl)-1-propenyl]-1H-imidazole isomer b, 4-[3-(4-cyanophenyl)-1-(4-fluorophenyl)- 1-propenyl]-1H-imidazole or a stereoisomer thereof, or non-toxic pharmaceutically acceptable acid addition salt thereof.

22. A method of inhibiting aromatase comprising administering to a subject in which such inhibition is desired, an aamount of a compound as claimed in claim 12 to produce the desired inhibition.

23. A pharmaceutical composition comprising an aromarase inhibiting amount of a compound as claimed in claim 12 and a pharmaceutically acceptable carrier.

24. A method of inhibiting aromatase comprising administering to a subject in which such inhibition is desired, an aamount of a composition as claimed in claim 23 to produce the desired inhibition.

* * * * *